United States Patent
Couto

(10) Patent No.: US 12,359,239 B2
(45) Date of Patent: Jul. 15, 2025

(54) RELATIVE POTENCY ASSAY FOR VIRAL VECTOR ENCODING ISOMEROHYDROLASES

(71) Applicant: SPARK THERAPEUTICS, INC., Philadelphia, PA (US)

(72) Inventor: Linda Couto, Pleasanton, CA (US)

(73) Assignee: Spark Therapeutics, Inc., Philadelphia, PA (US)

( * ) Notice: Subject to any disclaimer, the term of this patent is extended or adjusted under 35 U.S.C. 154(b) by 735 days.

(21) Appl. No.: 16/096,673

(22) PCT Filed: Apr. 28, 2017

(86) PCT No.: PCT/US2017/030254
§ 371 (c)(1),
(2) Date: Oct. 25, 2018

(87) PCT Pub. No.: WO2017/190081
PCT Pub. Date: Nov. 2, 2017

(65) Prior Publication Data
US 2021/0348210 A1      Nov. 11, 2021

Related U.S. Application Data

(60) Provisional application No. 62/328,916, filed on Apr. 28, 2016.

(51) Int. Cl.
C12Q 1/34      (2006.01)
B01D 15/32      (2006.01)
(Continued)

(52) U.S. Cl.
CPC ............ *C12Q 1/34* (2013.01); *B01D 15/325* (2013.01); *B01D 15/3819* (2013.01); *C12Q 1/44* (2013.01); *C12Y 301/01064* (2013.01); *C12N 15/86* (2013.01); *C12N 2750/14141* (2013.01); *G01N 2333/918* (2013.01); *G01N 2800/164* (2013.01)

(58) Field of Classification Search
None
See application file for complete search history.

(56) References Cited

U.S. PATENT DOCUMENTS 6,071,410 A * 6/2000 Nau .................. B01J 20/28078
210/656
7,951,841 B2 * 5/2011 Palczewski ............... A61P 3/02
514/529

(Continued)

FOREIGN PATENT DOCUMENTS

KR   10-2003-0074687 A   9/2003
KR   10-2008-0075832 A   8/2008
(Continued)

OTHER PUBLICATIONS

Golczak et al., "Molecular Biology and Analytical Chemistry Methods Used to Probe the Retinoid Cycle," Methods Mol Biol, 652: 229-245 (Year: 2015).*
Kane et al., "Quantification of Endogenous Retinoids," Methods Mol Biol 652: 1-54 (Year: 2010).*
Taylor et al., "Interpretation of the Correlation Coefficient: A Basic Review," Journal of Diagnostic Medical Sonography, vol. 6, No. 1: 35-39 (Year: 1990).*

(Continued)

*Primary Examiner* — M Franco G Salvoza
(74) *Attorney, Agent, or Firm* — Ice Miller LLP

(57) ABSTRACT

Methods for assaying function and/or activity and/or potency of isomerohydrolase proteins are provided.

50 Claims, 19 Drawing Sheets

Specification includes a Sequence Listing.

(51) Int. Cl.
*B01D 15/38* (2006.01)
*C12Q 1/44* (2006.01)
*C12N 15/86* (2006.01)

(56) References Cited

U.S. PATENT DOCUMENTS

| | | | |
|---|---|---|---|
| 2008/0249042 A1* | 10/2008 | Moise | A61P 37/06 435/243 |
| 2009/0253117 A1 | 10/2009 | Cerda et al. | |
| 2014/0357611 A1* | 12/2014 | Palczewski | A61K 31/197 514/249 |
| 2018/0021458 A1* | 1/2018 | Smith | A61P 17/00 424/233.1 |

FOREIGN PATENT DOCUMENTS

| | | | |
|---|---|---|---|
| KR | 10-2010-0041223 A | | 5/2010 |
| KR | 10-2011-0121777 A | | 11/2011 |
| SU | 873121 A1 | | 10/1981 |
| WO | 2002/053108 | | 7/2002 |
| WO | 2006/063128 A2 | | 6/2006 |
| WO | 2007/111390 A1 | | 10/2007 |
| WO | 2015/184453 A1 | | 12/2015 |
| WO | WO-2016018816 A1 * | | 2/2016 ............ A61P 27/02 |

OTHER PUBLICATIONS

McBee, J.K., et al., Isomerizatoin of all-trans-Retinol to cis-Retinols in Bovine Retinal Pigment Epithelial Cells: Dependence on the Specificity of Retinoid-Binding Proteins, Biochemistry, Sep. 19, 2000, 39(37):11370-11380.

Golczak, M., et al., Lecithin: Retinol Acyl Transferase (Lrat) is Responsible for Amnidation of Retinylamine, Apotent Inhibitor of the Retinoid Cycle, The Journal of Biological Chemistry, 2005, 280(51):42263-42273.

Couto, et al., Potency Assay for AAV Vector Encoding Retinal Pigment Epithelial 65 Protein, ARVO 2016 Annual Meeting Abstracts, May 1, 2016 (May 1. 2016), Abstract 759 only.

Kiser, et al., Key enzymes of the retinoid (visual) cycle in vertebrate retina, Biochim. Biophys. Acta, Apr. 4, 2012, 1821:1-32.

Mandal, et al., Alpha-phenyl-N-tert-butylnitrone (PBN) prevents light-induced degeneration of the retina by inhibiting RPE65 protein isomerohydrolase activity, J.Biol .Chem., 2011, 286:32491-501.

Moiseyev, et al. RPE65 is the isomerohydrolase in the retinoid visual cycle, Proc. Natl. Acad. Sci. USA, 2005, 102:12413-8.

*Virtek Vision International Inc.*, v. *Assembly Guidance Systems, Inc., DBA Aligned Vison*, Case: 22-1998, Document: 48; Appeals from the USPTO, Patent Trial and Appeal Board No. IPR2021-00062 (Fed Cir. 2024) Decided Mar. 27, 2024.

* cited by examiner

LC-MS/MS of retinols
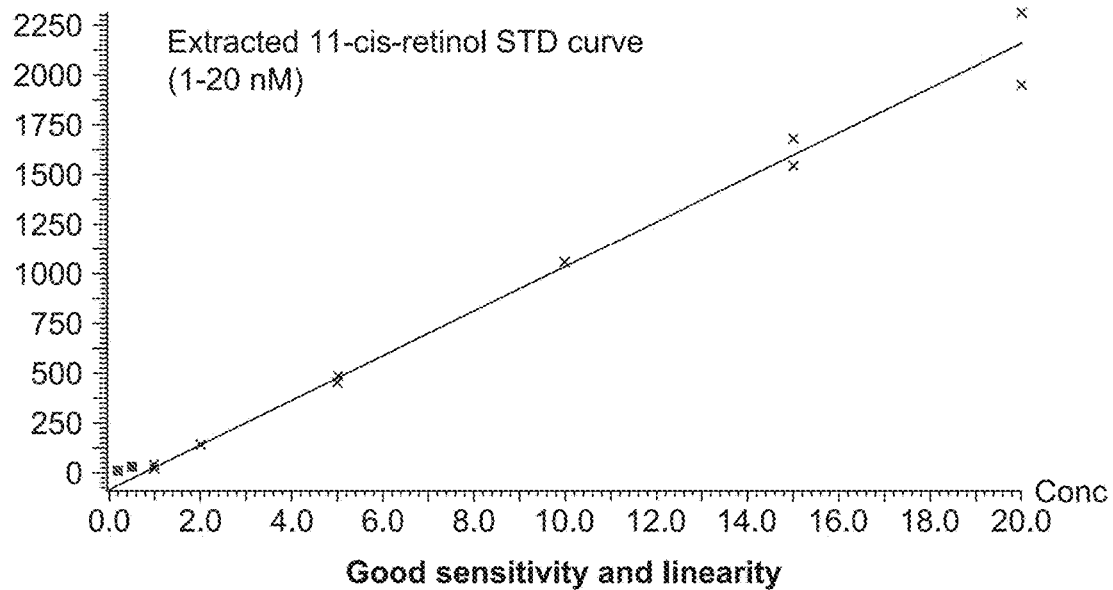
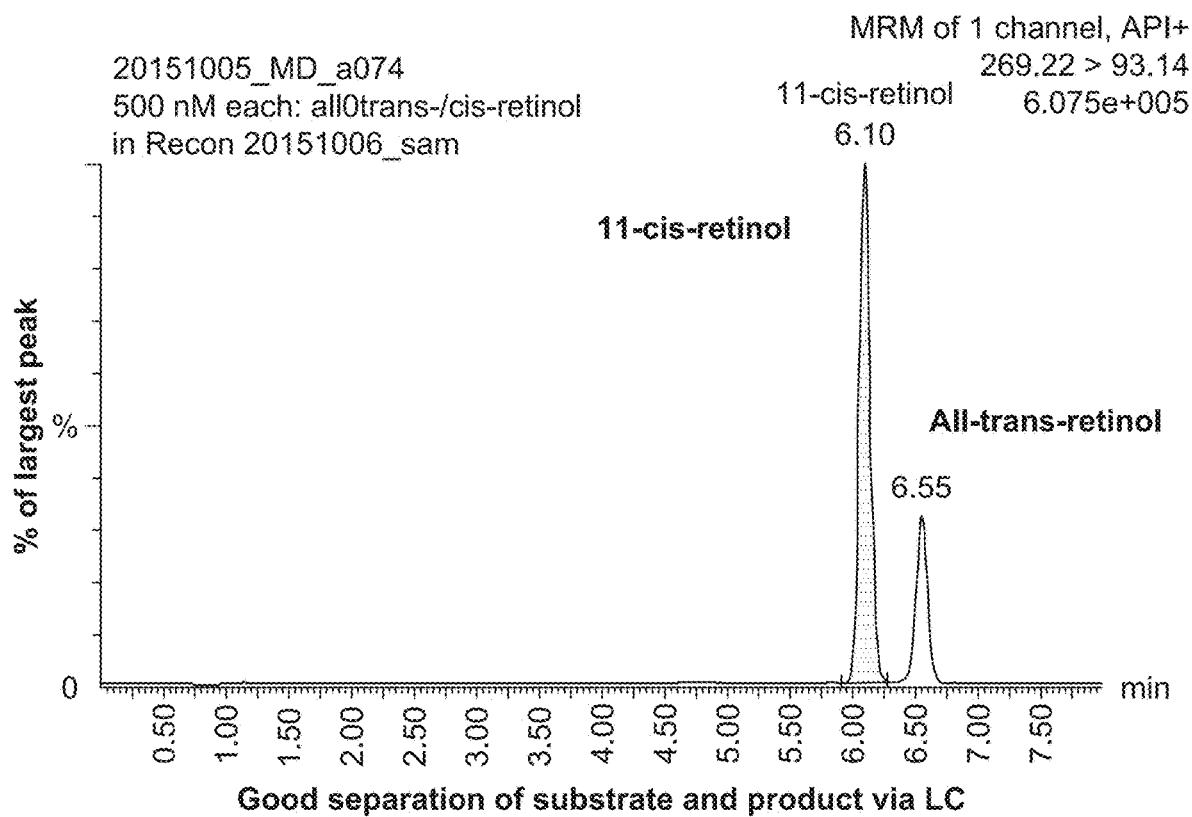
FIG. 3

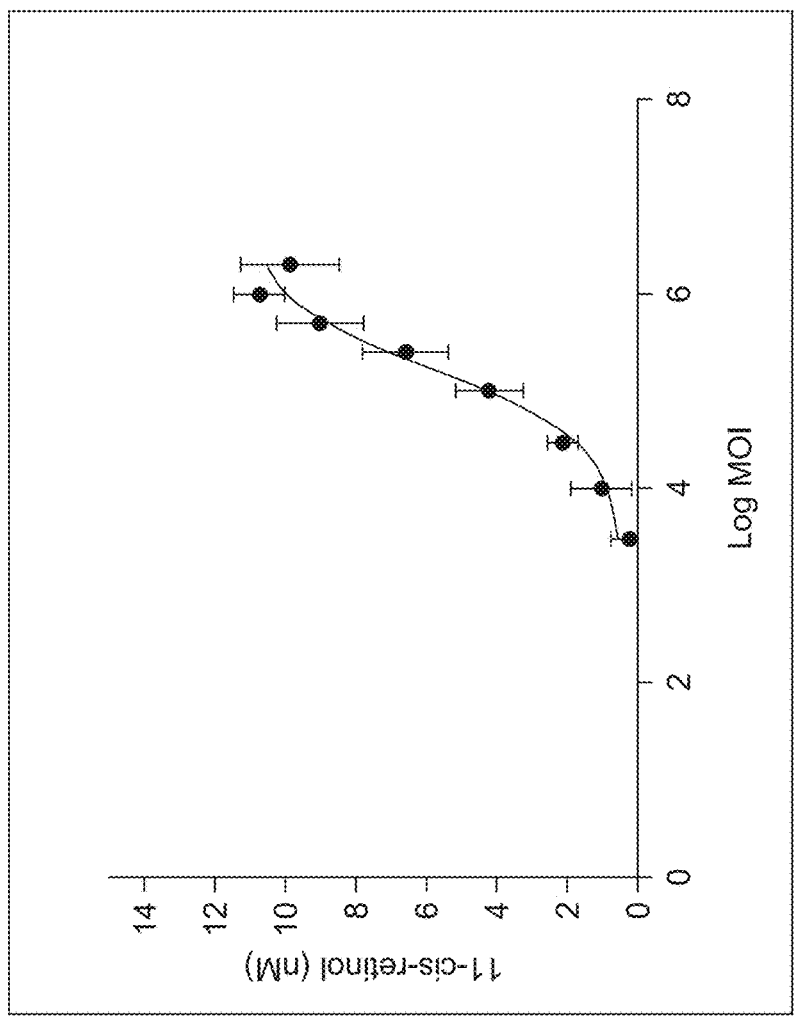

FIG. 6

Dose-dependent increase of of 11cROL over 8 MOIs of AAV-RPE65

Assay Design:
- HEK293/LRAT cells transduced with AAV-RPE65 vectors
- 8 MOIs ($3 \times 10^3$, $1 \times 10^4$, $3 \times 10^4$, $1 \times 10^5$, $2.5 \times 10^5$, $5 \times 10^5$, $1 \times 10^6$, $2 \times 10^6$ vector genomes/cell)
- Three independent transductions
- Cell lysates analyzed for RPE65 activity (3 assays/lysate)

| MOI | Ave | SD | CV |
|---|---|---|---|
| 3.00E+03 | BLOQ | | |
| 1.00E+04 | BLOQ | | |
| 3.00E+04 | 2.2 | 0.436 | 20.11% |
| 1.00E+05 | 4.2 | 0.944 | 22.33% |
| 2.50E+05 | 6.6 | 1.219 | 18.43% |
| 5.00E+05 | 9.0 | 1.218 | 13.47% |
| 1.00E+06 | 10.7 | 0.756 | 7.04% |
| 2.00E+06 | 9.9 | 1.386 | 14.02% |

Level 100%: _____

Plate 1 Vol. Sample: _____

| RS MOI 1.0 x 10^4 | RS MOI 1.0 x 10^4 | RS MOI 1.0 x 10^4 |
|---|---|---|
| TA MOI 1.0 x 10^4 | TA MOI 1.0 x 10^4 | TA MOI 1.0 x 10^4 |

Plate 2 Vol. Sample: _____

| RS MOI 2.0 x 10^4 | RS MOI 2.0 x 10^4 | RS MOI 2.0 x 10^4 |
|---|---|---|
| TA MOI 2.0 x 10^4 | TA MOI 2.0 x 10^4 | TA MOI 2.0 x 10^4 |

Plate 3 Vol. Sample: _____

| RS MOI 4.0 x 10^4 | RS MOI 4.0 x 10^4 | RS MOI 4.0 x 10^4 |
|---|---|---|
| TA MOI 4.0 x 10^4 | TA MOI 4.0 x 10^4 | TA MOI 4.0 x 10^4 |

Plate 4 Vol. Sample: _____

| RS MOI 6 x 10^4 | RS MOI 6 x 10^4 | RS MOI 6 x 10^4 |
|---|---|---|
| TA MOI 6 x 10^4 | TA MOI 6 x 10^4 | TA MOI 6 x 10^4 |

Plate 5 Vol. Sample: _____

| RS MOI 8.0 x 10^4 | RS MOI 8.0 x 10^4 | RS MOI 8.0 x 10^4 |
|---|---|---|
| TA MOI 8.0 x 10^4 | TA MOI 8.0 x 10^4 | TA MOI 8.0 x 10^4 |

Plate 6 Vol. Sample: _____

| RS MOI 1.6 x 10^5 | RS MOI 1.6 x 10^5 | RS MOI 1.6 x 10^5 |
|---|---|---|
| TA MOI 1.6 x 10^5 | TA MOI 1.6 x 10^5 | TA MOI 1.6 x 10^5 |

Plate 7 Vol. Sample: _____

| RS MOI 3.2 x 10^5 | RS MOI 3.2 x 10^5 | RS MOI 3.2 x 10^5 |
|---|---|---|
| TA MOI 3.2 x 10^5 | TA MOI 3.2 x 10^5 | TA MOI 3.2 x 10^5 |

Plate 8 Vol. Sample: _____

| RS MOI 6.4 x 10^5 | RS MOI 6.4 x 10^5 | RS MOI 6.4 x 10^5 |
|---|---|---|
| TA MOI 6.4 x 10^5 | TA MOI 6.4 x 10^5 | TA MOI 6.4 x 10^5 |

Plate 9 Vol. Sample: _____

| RS MOI 1.28 x 10^6 | RS MOI 1.28 x 10^6 | RS MOI 1.28 x 10^6 |
|---|---|---|
| TA MOI 1.28 x 10^6 | TA MOI 1.28 x 10^6 | TA MOI 1.28 x 10^6 |

Plate 10 Vol. Form Buf: _____

| Blank Matrix Control | Blank Matrix Control | Blank Matrix Control |
|---|---|---|
| No Transduction Control | No Transduction Control | Cell Count Well |

FIG. 10

Level 50%

Plate 1 Vol. Sample: _____

| RS MOI<br>1.0 x 10^4 | RS MOI<br>1.0 x 10^4 | RS MOI<br>1.0 x 10^4 |
|---|---|---|
| TA MOI<br>5.0 x 10^3 | TA MOI<br>5.0 x 10^3 | TA MOI<br>5.0 x 10^3 |

Plate 2 Vol. Sample: _____

| RS MOI<br>2.0 x 10^4 | RS MOI<br>2.0 x 10^4 | RS MOI<br>2.0 x 10^4 |
|---|---|---|
| TA MOI<br>1.0 x 10^4 | TA MOI<br>1.0 x 10^4 | TA MOI<br>1.0 x 10^4 |

Plate 3 Vol. Sample: _____

| RS MOI<br>4.0 x 10^4 | RS MOI<br>4.0 x 10^4 | RS MOI<br>4.0 x 10^4 |
|---|---|---|
| TA MOI<br>2.0 x 10^4 | TA MOI<br>2.0 x 10^4 | TA MOI<br>2.0 x 10^4 |

Plate 4 Vol. Sample: _____

| RS MOI<br>6 x 10^4 | RS MOI<br>6 x 10^4 | RS MOI<br>6 x 10^4 |
|---|---|---|
| TA MOI<br>3.0 x 10^4 | TA MOI<br>3.0 x 10^4 | TA MOI<br>3.0 x 10^4 |

Plate 5 Vol. Sample: _____

| RS MOI<br>8.0 x 10^4 | RS MOI<br>8.0 x 10^4 | RS MOI<br>8.0 x 10^4 |
|---|---|---|
| TA MOI<br>4.0 x 10^4 | TA MOI<br>4.0 x 10^4 | TA MOI<br>4.0 x 10^4 |

Plate 6 Vol. Sample: _____

| RS MOI<br>1.6 x 10^5 | RS MOI<br>1.6 x 10^5 | RS MOI<br>1.6 x 10^5 |
|---|---|---|
| TA MOI<br>8.0 x 10^4 | TA MOI<br>8.0 x 10^4 | TA MOI<br>8.0 x 10^4 |

Plate 7 Vol. Sample: _____

| RS MOI<br>3.2 x 10^5 | RS MOI<br>3.2 x 10^5 | RS MOI<br>3.2 x 10^5 |
|---|---|---|
| TA MOI<br>1.6 x 10^5 | TA MOI<br>1.6 x 10^5 | TA MOI<br>1.6 x 10^5 |

Plate 8 Vol. Sample: _____

| RS MOI<br>6.4 x 10^5 | RS MOI<br>6.4 x 10^5 | RS MOI<br>6.4 x 10^5 |
|---|---|---|
| TA MOI<br>3.2 x 10^5 | TA MOI<br>3.2 x 10^5 | TA MOI<br>3.2 x 10^5 |

Plate 9 Vol. Sample: _____

| RS MOI<br>1.28 x 10^6 | RS MOI<br>1.28 x 10^6 | RS MOI<br>1.28 x 10^6 |
|---|---|---|
| TA MOI<br>6.4 x 10^5 | TA MOI<br>6.4 x 10^5 | TA MOI<br>6.4 x 10^5 |

Plate 10 Vol. Form Buf: _____

| Blank<br>Matrix<br>Control | Blank<br>Matrix<br>Control | Blank<br>Matrix<br>Control |
|---|---|---|
| No<br>Transduction Control | No<br>Transduction Control | Cell Count<br>Well |

Level 150%

| Plate 1 Vol. Sample: | | |
|---|---|---|
| RS MOI 1.0 x 10^4 | RS MOI 1.0 x 10^4 | RS MOI 1.0 x 10^4 |
| TA MOI 1.5 x 10^4 | TA MOI 1.5 x 10^4 | TA MOI 1.5 x 10^4 |

| Plate 2 Vol. Sample: | | |
|---|---|---|
| RS MOI 2.0 x 10^4 | RS MOI 2.0 x 10^4 | RS MOI 2.0 x 10^4 |
| TA MOI 3.0 x 10^4 | TA MOI 3.0 x 10^4 | TA MOI 3.0 x 10^4 |

| Plate 3 Vol. Sample: | | |
|---|---|---|
| RS MOI 4.0 x 10^4 | RS MOI 4.0 x 10^4 | RS MOI 4.0 x 10^4 |
| TA MOI 6.0 x 10^4 | TA MOI 6.0 x 10^4 | TA MOI 6.0 x 10^4 |

| Plate 4 Vol. Sample: | | |
|---|---|---|
| RS MOI 6 x 10^4 | RS MOI 6 x 10^4 | RS MOI 6 x 10^4 |
| TA MOI 9.0 x 10^4 | TA MOI 9.0 x 10^4 | TA MOI 9.0 x 10^4 |

| Plate 5 Vol. Sample: | | |
|---|---|---|
| RS MOI 8.0 x 10^4 | RS MOI 8.0 x 10^4 | RS MOI 8.0 x 10^4 |
| TA MOI 1.2 x 10^5 | TA MOI 1.2 x 10^5 | TA MOI 1.2 x 10^5 |

| Plate 6 Vol. Sample: | | |
|---|---|---|
| RS MOI 1.6 x 10^5 | RS MOI 1.6 x 10^5 | RS MOI 1.6 x 10^5 |
| TA MOI 2.4 x 10^5 | TA MOI 2.4 x 10^5 | TA MOI 2.4 x 10^5 |

| Plate 7 Vol. Sample: | | |
|---|---|---|
| RS MOI 3.2 x 10^5 | RS MOI 3.2 x 10^5 | RS MOI 3.2 x 10^5 |
| TA MOI 4.8 x 10^5 | TA MOI 4.8 x 10^5 | TA MOI 4.8 x 10^5 |

| Plate 8 Vol. Sample: | | |
|---|---|---|
| RS MOI 6.4 x 10^5 | RS MOI 6.4 x 10^5 | RS MOI 6.4 x 10^5 |
| TA MOI 9.6 x 10^5 | TA MOI 9.6 x 10^5 | TA MOI 9.6 x 10^5 |

| Plate 9 Vol. Sample: | | |
|---|---|---|
| RS MOI 1.28 x 10^6 | RS MOI 1.28 x 10^6 | RS MOI 1.28 x 10^6 |
| TA MOI 1.92 x 10^6 | TA MOI 1.92 x 10^6 | TA MOI 1.92 x 10^6 |

| Plate 10 Vol. Form Buf.: | | |
|---|---|---|
| Blank Matrix Control | Blank Matrix Control | Blank Matrix Control |
| No Transduction Control | No Transduction Control | Cell Count Well |

RELATIVE POTENCY ASSAY FOR VIRAL VECTOR ENCODING ISOMEROHYDROLASES

RELATED APPLICATIONS

This patent application is the National Phase of International Application No. PCT/US2017/030254, filed Apr. 28, 2017, which designated the U.S. and that International Application was published under PCT Article 21(2) in English, which claims the benefit of priority to U.S. Provisional Patent Application No. 62/328,916, filed Apr. 28, 2016. The entire contents of the foregoing applications are incorporated herein by reference, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Oct. 25, 2018, is named "Spark0501183ST25.txt" and is 4.87 KB in size.

INTRODUCTION

Isomerohydrolase activity or potency can be measured by quantifying reaction products produced by such enzymes. The invention relates to measuring isomerohydrolase activity and/or potency.

SUMMARY

The invention provides methods for measuring and/or detecting isomerohydrolase activity. In certain embodiments, methods include the use of a non-radioactive isomerohydrolase substrate or precursor of the isomerohydrolase substrate and detection of the non-radioactive reaction product produced by conversion by the isomerohydrolase. In certain embodiments, methods include the use of mass spectrometry to quantify the reaction product thereby measuring and/or detecting isomerohydrolase activity.

In a particular embodiment, a method for measuring and/or detecting isomerohydrolase activity includes (a) contacting cells (e.g., eukaryotic cells) expressing Lecithin Retinol Acyltransferase (LRAT) with a viral vector (e.g., an adeno-associated viral (AAV) vector) comprising a transgene encoding an isomerohydrolase protein (e.g., RPE65) under conditions allowing cell transduction; incubating viral vector transduced cells under conditions allowing expression of the encoded isomerohydrolase protein (e.g., RPE65); lysing the transduced cells to produce an extract (e.g., cell extract) comprising the encoded isomerohydrolase protein; incubating the extract (e.g., cell extract) with a substrate for a period of time and under conditions allowing conversion of the substrate by the isomerohydrolase protein to a reaction product; subjecting the reaction product to column (liquid) chromatography thereby producing a column (liquid) chromatography purified reaction product; and subjecting said column (liquid) chromatography purified reaction product to mass spectrometry thereby quantifying the reaction product, wherein the amount of reaction product reflects isomerohydrolase activity thereby measuring isomerohydrolase activity.

In various embodiments, the isomerohydrolase protein comprises retinal pigment epithelium-specific protein, 65-KD (RPE65). In various embodiments, the isomerohydrolase protein comprises wild-type retinal pigment epithelium-specific protein, 65-KD (RPE65). In various embodiments, the isomerohydrolase protein comprises a variant or mutant retinal pigment epithelium-specific protein, 65-KD (RPE65). In various embodiments, the isomerohydrolase protein comprises a mammalian retinal pigment epithelium-specific protein, 65-KD (RPE65). In various embodiments, the isomerohydrolase protein comprises a human retinal pigment epithelium-specific protein, 65-KD (RPE65).

In various embodiments, the cells transduced comprise mammalian cells. In various embodiments, the cells transduced comprise human cells. In various embodiments, the cells transduced comprise Human Embryonic Kidney (HEK) 293 cells.

In various embodiments, the cells transduced express LRAT stably or transiently. In various embodiments, the cells transduced express CRALBP stably or transiently. In various embodiments, the cells transduced express LRAT and/or CRALBP stably or transiently.

In various embodiments, the substrate comprises all-trans-retinyl ester.

In various embodiments, the step (d) comprises adding a precursor of the substrate to the extract, wherein the precursor is converted to the substrate by the expressed LRAT. In various embodiments, the step (d) comprises adding cellular retinaldehyde binding protein (CRALBP) and a precursor of the substrate to the extract, wherein the precursor is converted to the substrate by the expressed LRAT.

In various embodiments, the amount of CRALBP added is between about 50 and about 500 µg.

In various embodiments, the precursor comprises or consists of all-trans retinol. In various embodiments, the precursor, such as the all-trans retinol, is added such that the final concentration is from about 1 to about 20 mM.

In various embodiments, the reaction product comprises or consists of 11-cis-retinol.

In various embodiments, the step (d), (e) and/or (f) is performed in the dark, under dim light or under dim yellow light.

In various embodiments, the substrate, precursor or reaction product is non-radioactive.

In various embodiments, the period of time of step (d) is from about 30 minutes to about 240 minutes.

In various embodiments, after step (d) but before step (e) the reaction is stopped or quenched. In various embodiments, after step (d) but before step (e) an alcohol is added.

In various embodiments, wherein after step (d) but before step (e) the reaction product is extracted. In various embodiments, wherein after step (d) but before step (e) the reaction product is extracted with an organic solvent, such as with hexane.

In various embodiments, the method of any of steps (a)-(d) are performed as set forth in Example 1.

In various embodiments, the method of any of steps (e)-(f) are performed as set forth in Example 2.

In various embodiments, the adeno-associated viral (AAV) vector comprises a capsid protein sequence or inverted terminal repeat sequence having 70% or more sequence identity to a capsid protein sequence or to an inverted terminal repeat sequence of any serotype selected from AAV1, AAV2, AAV3, AAV4, AAV5, AAV6, AAV7, AAV8, AAV9, and AAV10.

In various embodiments, the adeno-associated viral (AAV) vector comprises a capsid protein or inverted terminal repeat of any serotype selected from AAV1, AAV2, AAV3, AAV4, AAV5, AAV6, AAV7, AAV8, AAV9, AAV10.

In various embodiments, the step (a) contacting cells is with an amount of about 500 to about 5 million AAV vector particles/cell. In various embodiments, the step (a) contacting cells is with an amount of about 1,000 to about 1,000,000 AAV vector particles/cell. In various embodiments, the step (a) contacting cells is with an amount of about 2,000 to about 500,000 AAV vector particles/cell.

In various embodiments, the step (b) comprises incubating the transduced cells for a time period from about 6 hours to about 96 hours.

In various embodiments, the lysing of the transduced cells of (c) is by way of freeze-thawing, sonication or a combination thereof.

In various embodiments, the amount of total cellular protein produced after step (c) is determined. In various embodiments, the amount of total cellular protein produced after step (c) is determined by a Bradford assay.

In various embodiments, the precursor is mixed with a 10-100% solution of DMF.

In various embodiments, after collecting cells but prior to step (c) lysing, the collected cells are resuspended in buffer.

In various embodiments, after step (c) lysing the collected cells to produce an extract, the extract is diluted in buffer.

In various embodiments, the buffer is a salt buffer. In various embodiments, the buffer is a NaCl buffer.

In various embodiments, the extract produced by step (c) comprises from about 10 μg to about 2,000 μg total cellular protein or is adjusted to be from about 10 μg to about 2,000 μg total protein.

In various embodiments, the extract produced by step (c) comprises from about 50 μg to about 750 μg total cellular protein or is adjusted to be from about 50 μg to about 750 μg total protein.

In various embodiments, wherein the step (d) incubating is at a temperature from about 30 to about 40° C.

In various embodiments, the column chromatography separates 11-cis-retinol from 9-cis-retinol and/or separates 11-cis-retinol from 13-cis-retinol.

In various embodiments, the column chromatography comprises reverse-phase chromatography. In various embodiments, the column chromatography comprises a reverse-phase stationary phase.

In various embodiments, the stationary phase comprises a C18 chain. In various embodiments, the stationary phase comprises a hydrophilic group. In various embodiments, the hydrophilic group comprises a carbamate group. In various embodiments, the stationary phase comprises a hydrophilic carbamate group within a C18 chain. In various embodiments, the phase comprises a silylcarbamate group.

In various embodiments, the method is linear from about $1\times10^4$ to about $2\times10^6$ AAV vector genomes per cell.

In various embodiments, the method coefficient of determination ($R^2$) is greater than about 0.85.

DESCRIPTION OF DRAWINGS

FIG. 3 shows a standard curve (top panel) and elution profile of 11-cis-retinol by liquid chromatography.

FIG. 6 shows increased 11-cis-retinol production with increased AAV-RPE65 MOI. 8 different MOIs evaluated. BLOQ=below level of quantitation. SD=standard deviation. CV=coefficient variant.

FIG. 10 shows Analyst 1 (or Analyst 2), Prep 1, Example Plate Map for 9 MOI, Analytical Reference Standard vs Sample (Test Article) (Level 100% Accuracy).

FIG. 11 shows Analyst 1 (or Analyst 2), Prep 1, Example Plate Map for 9 MOI, Analytical Reference Standard vs Sample (Test Article) (Level 50% Accuracy).

FIG. 12 shows Analyst 1 (or Analyst 2), Prep 1, Example Plate Map for 9 MOI, Analytical Reference Standard vs Sample (Test Article) (Level 150% Accuracy).

DETAILED DESCRIPTION

Figure 1:
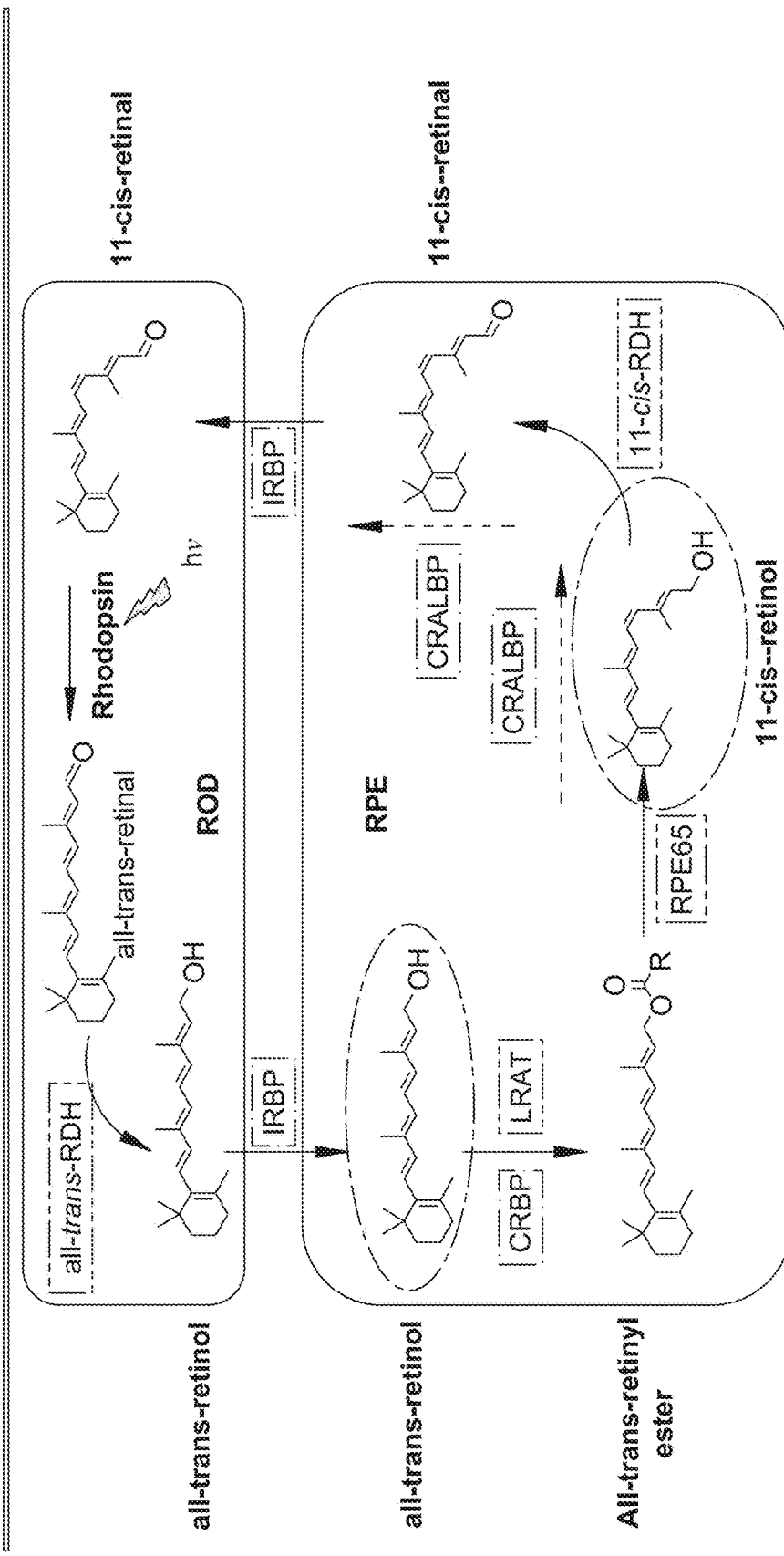
FIG. 1 shows an overview of RPE65 function in the Visual Cycle
Figure 2:
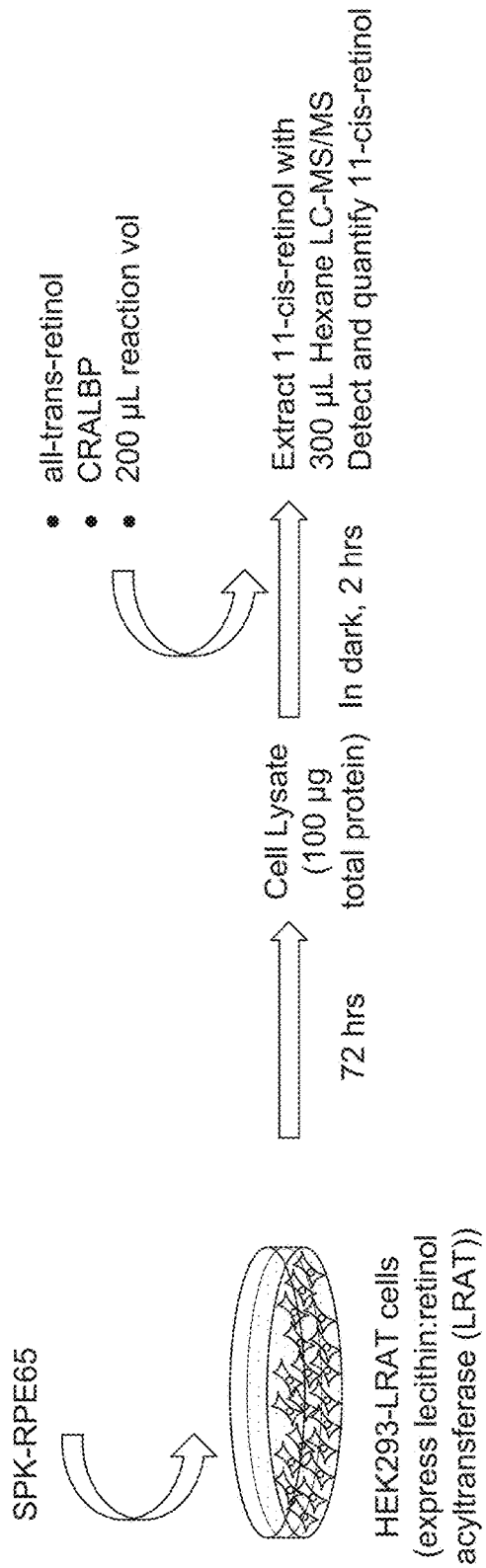
FIG. 2 summarizes the overall vector based RPE65 potency assay. 11-cis-retinol is extracted with the hexane and subsequently analyzed by liquid chromatography/mass spectrometry.
Figure 4:
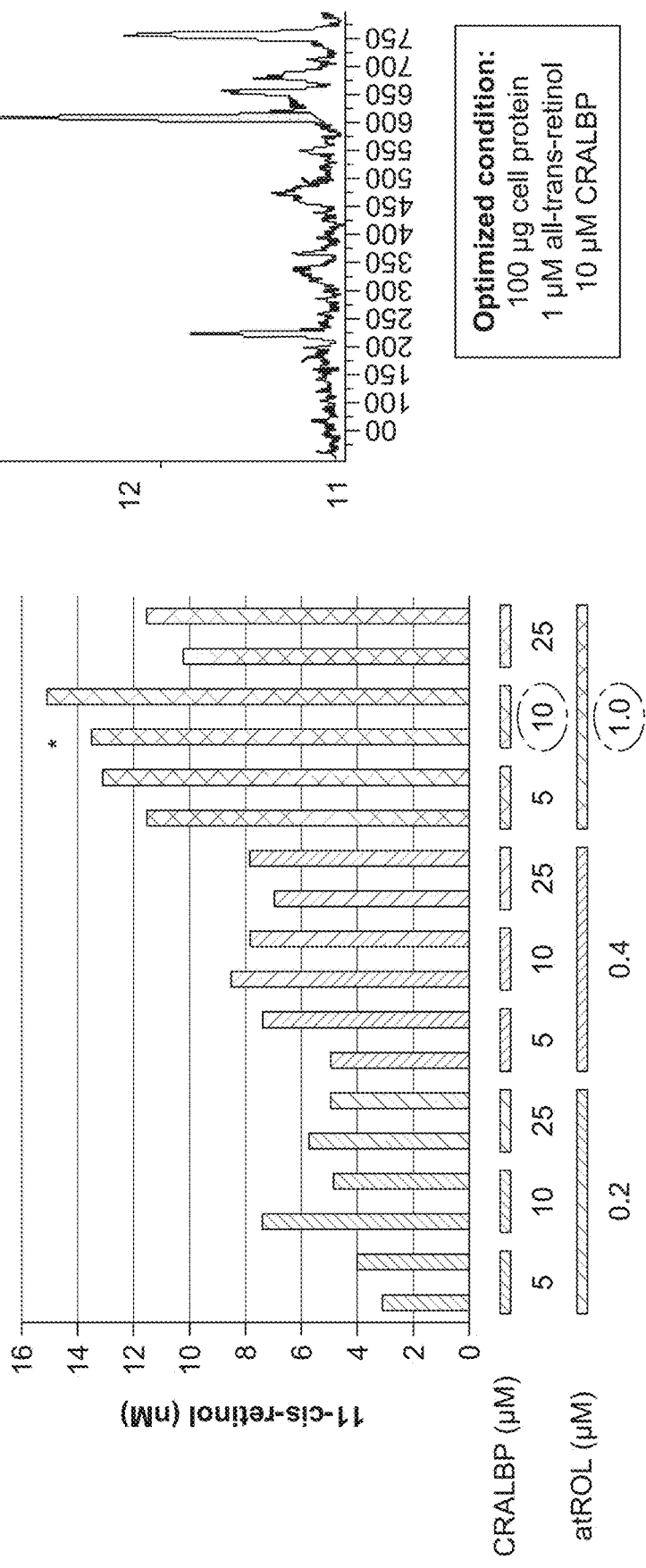
FIG. 4 shows optimization of CRALBP and all trans retinol (atROL) by evaluating various concentrations. In this assay, optimal CRALBP is 10 μM and optimal atROL is 1.0 μM.
Figure 5:
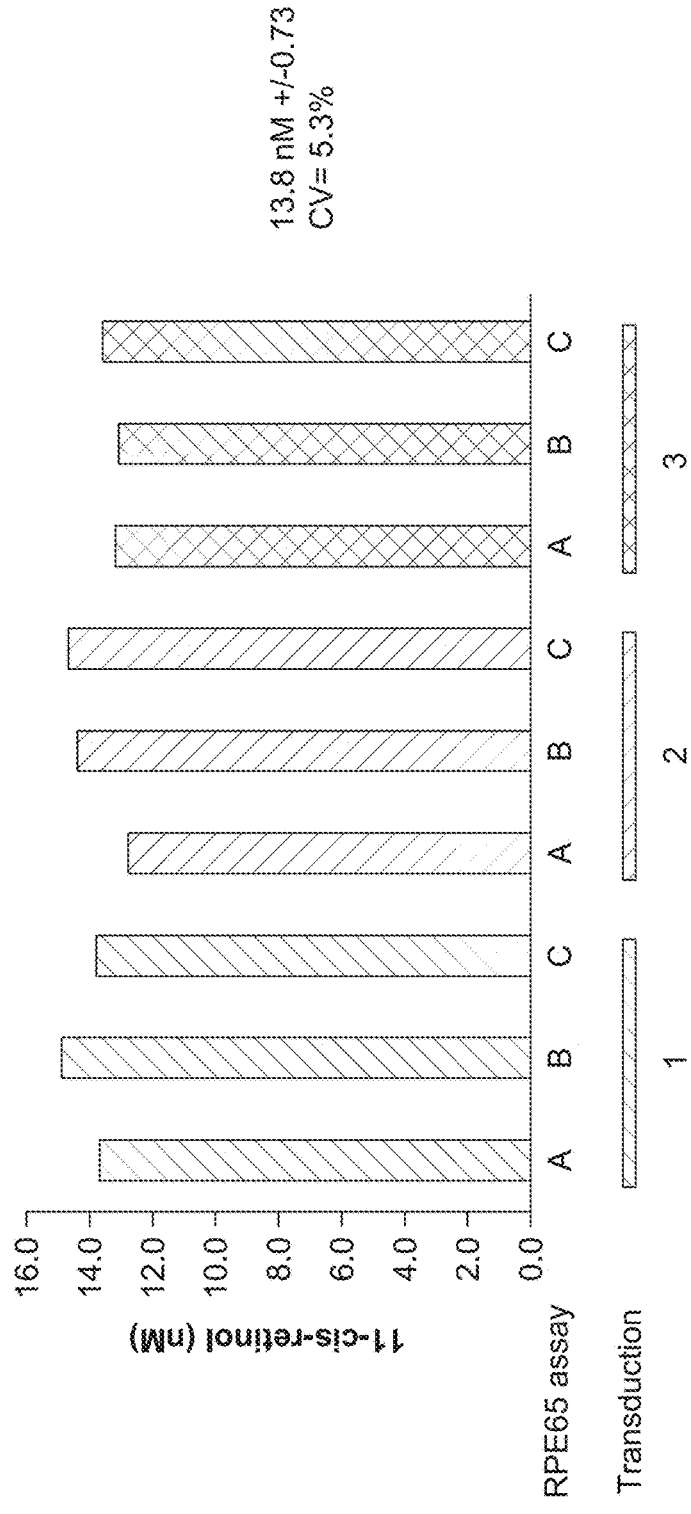
FIG. 5 shows reproducibility of the assay with 9 total assays of RPE65.
Figure 7:
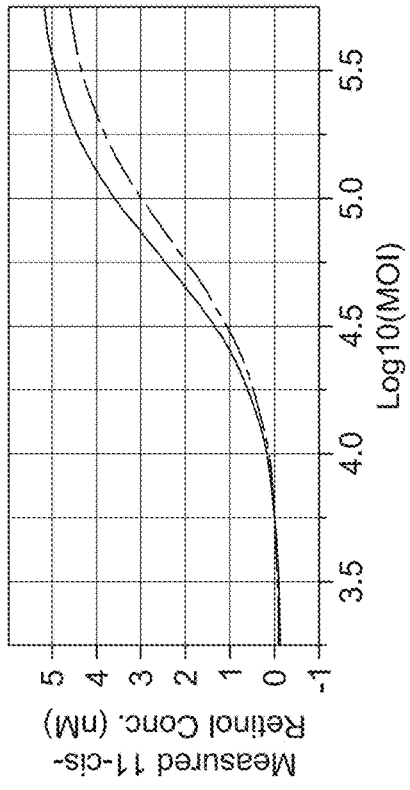
FIG. 7 shows 11-cis-retinol analysis from two different AAV-RPE65 vector lots at five different MOIs.

The invention provides methods for measuring and/or detecting isomerohydrolase protein activity and/or function. In various embodiments, the methods are specific (non-interference of buffer), has dilutional linearity, are accurate and has precision over a broad range of multiplicity of infection (MOI). For example, the range of 50% to 150% of the nominal method concentrations, multiplicity of infection (MOI) 1.00E+04, 2.00E+04, 4.00E+04, 6.00E+04, 8.00E+04, 1.60E+05, 3.20E+05, 6.40E+05, 1.28E+06 vector genomes (vg) per cell, is supported by linearity, accuracy and precision data.

Invention methods for measuring and/or detecting isomerohydrolase protein activity and/or function set forth herein include methods qualified for testing both drug substance (DS) and drug product (DP). System suitability criteria were met for each analytical set. Invention methods include methods shown to be suitable for its intended purpose.

Isomerohydrolase nucleic acid and protein sequences useful in the invention include retinoid isomerohydrolase, such as Retinal pigment epithelium-specific 65 kDa protein (RPE65). Retinoid isomerohydrolase, also referred to as all-trans-retinyl-palmitate hydrolase and Retinol Isomerase among other synonyms, is involved in the synthesis of 11-cis-retinol. (RPE65) is an enzyme of the vertebrate visual cycle that is responsible for isomerohydrolase activity, or converting all-trans-retinyl ester to 11-cis-retinol (Moiseyev, et. al. 2005). All-trans-retinol (atROL) is esterified by lecithin: retinol acyl-transferase (LRAT), then the ester is presented to RPE65 for the isomerization reaction (Moiseyev, et. al. 2003).

Diseases associated with Rpe65 deficiency include, for example, Leber's Congenital Amaurosis and Retinitis Pigmentosa 20.

Representative human RPE65 protein is set forth as:

```
                                            (SEQ ID NO: 1)
MSIQVEHPAG GYKKLFETVE ELSSPLTAHV TGRIPLWLTG

SLLRCGPGLF EVGSEPFYHL FDGQALLHKF DFKEGHVTYH

RRFIRTDAYV RAMTEKRIVI TEFGTCAFPD PCKNIFSRFF

SYFRGVEVTD NALVNVYPVG EDYYACTETN FITKINPETL

ETIKQVDLCN YVSVNGATAH PHIENDGTVY NIGNCFGKNF

SIAYNIVKIP PLQADKEDPI SKSEIVVQFP CSDRFKPSYV

HSFGLTPNYI VFVETPVKIN LFKFLSSWSL WGANYMDCFE

SNETMGVWLH IADKKRKKYL NNKYRTSPFN LFHHINTYED

NGFLIVDLCC WKGFEFVYNY LYLANLRENW EEVKKNARKA

PQPEVRRYVL PLNIDKADTG KNLVTLPNTT ATAILCSDET

IWLEPEVLFS GPRQAFEFPQ INYQKYCGKP YTYAYGLGLN

HFVPDRLCKL NVKTKETWVW QEPDSYPSEP IFVSHPDALE

EDDGVVLSVV VSPGAGQKPA YLLILNAKDL SEVARAEVEI

NIPVTFHGLFKKS
```

Additional RPE65 proteins include variants, such as those disclosed in WO2016018816A1, which is incorporated herein by reference.

The term "vector" refers to small carrier nucleic acid molecule, a plasmid, virus (e.g., AAV vector), or other vehicle that can be manipulated by insertion or incorporation of a nucleic acid. Vectors can be used for genetic manipulation (i.e., "cloning vectors"), to introduce/transfer polynucleotides into cells, and to transcribe or translate the inserted polynucleotide in cells. An "expression vector" is a vector that contains a gene or nucleic acid sequence with the necessary regulatory regions needed for expression in a host cell. A vector nucleic acid sequence generally contains at least an origin of replication for propagation in a cell and optionally additional elements, such as a isomerohydrolase nucleic acid sequence, expression control element (e.g., a promoter, enhancer), intron, inverted terminal repeats (ITRs), optional selectable marker, polyadenylation signal.

An AAV vector is derived from adeno-associated virus. AAV vectors are useful as gene therapy vectors as they can penetrate cells and introduce nucleic acid/genetic material so that the nucleic acid/genetic material may be stably maintained in cells. In addition, these viruses can introduce nucleic acid/genetic material into specific sites, for example, such as a specific site on chromosome 19. Because AAV are not associated with pathogenic disease in humans, AAV vectors are able to deliver heterologous nucleic acid sequences (e.g., therapeutic proteins and agents) to human patients without causing substantial AAV pathogenesis or disease.

The term "recombinant," as a modifier of vector, such as rAAV vectors, as well as a modifier of sequences such as recombinant polynucleotides and polypeptides, means that the compositions have been manipulated (i.e., engineered) in a fashion that generally does not occur in nature. A particular example of a recombinant AAV vector would be where a nucleic acid, such as isomerohydrolase, that is not normally present in the wild-type AAV genome is inserted within the viral genome. Although the term "recombinant" is not always used herein in reference to AAV vectors, as well as sequences such as polynucleotides, recombinant forms including AAV vectors, polynucleotides, isomerohydrolases, etc., are expressly included in spite of any such omission.

A "rAAV vector" is derived from the wild type genome of a virus, such as AAV by using molecular methods to remove the wild type genome from AAV genome, and replacing with a non-native (heterologous) nucleic acid, such as a nucleic acid encoding an isomerohydrolase. Typically, for AAV one or both inverted terminal repeat (ITR) sequences of AAV genome are retained in the rAAV vector. A rAAV is distinguished from an AAV genome since all or a part of the AAV genome has been replaced with a non-native sequence with respect to the AAV genomic nucleic acid, such as with a heterologous nucleic acid encoding an isomerohydrolase. Incorporation of a non-native sequence therefore defines the AAV as a "recombinant" AAV vector, which can be referred to as a "rAAV vector."

A recombinant AAV vector sequence can be packaged—referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV" or "rAAV particle" or "rAAV virion." Such rAAV, rAAV particles and rAAV virions include proteins that encapsidate or package the vector genome. Particular examples include in the case of AAV, capsid proteins.

A vector "genome" refers to the portion of the recombinant plasmid sequence that is ultimately packaged or encapsidated to form a rAAV particle. In cases where recombinant plasmids are used to construct or manufacture recombinant AAV vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsidated into rAAV particles. Thus, a vector "genome" refers to the nucleic acid that is packaged or encapsidated by rAAV.

"AAV helper functions" refer to AAV-derived coding sequences (proteins) which can be expressed to provide AAV gene products and AAV vectors that, in turn, function in trans for productive AAV replication and packaging. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products (capsids) supply necessary packaging functions. AAV helper functions are used to complement AAV functions in trans that are missing from AAV vector genomes.

An "AAV helper construct" refers generally to a nucleic acid sequence that includes nucleotide sequences providing AAV functions deleted from an AAV vector which is to be used to produce a transducing AVV vector for delivery of a nucleic acid sequence of interest, by way of gene therapy to a subject, for example. AAV helper constructs are commonly used to provide transient expression of AAV rep and/or cap genes to complement missing AAV functions that are necessary for AAV vector replication. Helper constructs generally lack AAV ITRs and can neither replicate nor package themselves. AAV helper constructs can be in the form of a plasmid, phage, transposon, cosmid, virus, or virion. A number of AAV helper constructs have been described, such as plasmids pAAV/Ad and pIM29+45 which encode both Rep and Cap expression products (See, e.g., Samulski et al. (1989) J. Virol. 63:3822-3828; and McCarty et al. (1991) J. Virol. 65:2936-2945). A number of other vectors have been described which encode Rep and/or Cap expression products (See, e.g., U.S. Pat. Nos. 5,139,941 and 6,376,237).

The term "accessory functions" refers to non-AAV derived viral and/or cellular functions upon which AAV is dependent for replication. The term includes proteins and RNAs that are required in AAV replication, including moieties involved in activation of AAV gene transcription, stage specific AAV mRNA splicing, AAV DNA replication, synthesis of Cap expression products and AAV capsid packaging. Viral-based accessory functions can be derived from any of the known helper viruses such as adenovirus, herpesvirus (other than herpes simplex virus type-1) and vaccinia virus.

An "accessory function vector" refers generally to a nucleic acid molecule that includes polynucleotide sequences providing accessory functions. Such sequences can be on an accessory function vector, and transfected into a suitable host cell. The accessory function vector is capable of supporting rAAV virion production by the host cell. Accessory function vectors can be in the form of a plasmid, phage, transposon or cosmid. In addition, the full-complement of adenovirus genes are not required for accessory functions. For example, adenovirus mutants incapable of DNA replication and late gene synthesis have been reported to be permissive for AAV replication (Ito et al., (1970) J. Gen. Virol. 9:243; Ishibashi et al, (1971) Virology 45:317). Similarly, mutants within E2B and E3 regions have been shown to support AAV replication, indicating that the E2B and E3 regions are probably not involved in providing accessory functions (Carter et al., (1983) Virology 126:505). Adenoviruses defective in the E1 region, or having a deleted E4 region, are unable to support AAV replication. Thus, E1A and E4 regions appear necessary for AAV replication, either directly or indirectly (Laughlin et al., (1982) J. Virol. 41:868; Janik et al., (1981) Proc. Natl. Acad. Sci. USA 78:1925; Carter et al., (1983) Virology 126:505). Other characterized Adenovirus mutants include: E1B (Laughlin et al. (1982), supra; Janik et al. (1981), supra; Ostrove et al., (1980) Virology 104:502); E2A (Handa et al., (1975) J. Gen. Virol. 29:239; Strauss et al., (1976) J. Virol. 17:140; Myers et al., (1980) J. Virol. 35:665; Jay et al., (1981) Proc. Natl. Acad. Sci. USA 78:2927; Myers et al., (1981) J. Biol. Chem. 256:567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)). Studies of the accessory functions provided by adenoviruses having mutations in the E1B coding region have produced conflicting results, but E1B55k may be required for AAV virion production, while E1B19k is not (Samulski et al., (1988) J. Virol. 62:206-210). In addition, International Publication WO 97/17458 and Matshushita et al., (1998) Gene Therapy 5:938-945, describe accessory function vectors encoding various Adenovirus genes. Exemplary accessory function vectors comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Such accessory function vectors are described, for example, in International Publication No. WO 01/83797.

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Cross-reactivity differences are usually due to differences in capsid protein sequences/antigenic determinants (e.g., due to VP1, VP2, and/or VP3 sequence differences of AAV serotypes).

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

rAAV vectors include any viral strain or serotype. As a non-limiting example, a rAAV plasmid or vector genome or particle (capsid protein) can be based upon any AAV serotype, such as AAV-1, -2, -3, -4, -5, -6, -7, -8, -9, -10, -11, for example. Such vectors can be based on the same of strain or serotype (or subgroup or variant), or be different from each other. As a non-limiting example, a rAAV plasmid or vector genome or particle (capsid) based upon one serotype genome can be identical to one or more of the capsid proteins that package the vector. In addition, a rAAV plasmid or vector genome can be based upon an AAV (e.g., AAV2) serotype genome distinct from one or more of the capsid proteins that package the vector genome, in which case at least one of the three capsid proteins could be a AAV1, AAV2, AAV3, AAV4, AAV5, AAV6, AAV7, AAV8, AAV9, AAV10, AAV11, or variant thereof, for example. rAAV vectors therefore include gene/protein sequences identical to gene/protein sequences characteristic for a particular serotype, as well as mixed serotypes.

In various exemplary embodiments, a rAAV vector includes or consists of a capsid sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 capsid proteins. In various exemplary embodiments, a rAAV vector includes or consists of a sequence at least 70% or more (e.g., 75%, 80%, 85%, 90%, 95%, 96%, 97%, 98%, 99%, 99.5%, etc.) identical to one or more AAV1, AAV2, AAV3, AAV4, AAV5, AAV6, AAV7, AAV8, AAV9, AAV10, or AAV11 inverted terminal repeats (ITRs).

rAAV, such as AAV1, AAV2, AAV3, AAV4, AAV5, AAV6, AAV7, AAV8, AAV9, AAV10, and AAV11, and variant, hybrid and chimeric sequences, can be constructed using recombinant techniques that are known to the skilled artisan, to include a heterologous polynucleotide (isomerohydrolase sequence) flanked with one or more functional AAV ITR sequences. Such vectors have one or more of the wild type AAV genes deleted in whole or in part, but retain at least one functional flanking ITR sequence(s), as necessary for the rescue, replication, and packaging of the recombinant vector into a rAAV vector particle. A rAAV vector genome would therefore include sequences required in cis for replication and packaging (e.g., functional ITR sequences)

Methods are known in the art for generating rAAV virions. For example, transfection using AAV vector and AAV helper sequences in conjunction with coinfection with AAV helper viruses (e.g., adenovirus, herpesvirus, or vaccinia virus) or transfection with a recombinant AAV vector, an AAV helper vector, and an accessory function vector. Non-limiting methods for generating rAAV virions are described, for example, in U.S. Pat. Nos. 6,001,650 and 6,004,797. Following recombinant rAAV vector production (i.e. vector generation in cell culture systems), rAAV virions can be obtained from the host cells and cell culture supernatant and optionally purified.

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids include naturally occurring, synthetic, and intentionally modified or altered polynucleotides. Nucleic acids can be single, double, or triplex, linear or circular, and can be of any length. In discussing nucleic acids, a sequence or structure of a particular polynucleotide may be described herein according to the convention of providing the sequence in the 5' to 3' direction.

A "host cell" denotes, for example, microorganisms, yeast cells, insect cells, and mammalian cells, that can be, or have been, used as recipients of an AAV vector plasmid, AAV helper construct, an accessory function vector, or other transfer DNA. The term includes the progeny of the original cell which has been transfected. Thus, a "host cell" generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. Exemplary host cells include human embryonic kidney (HEK) cells such as HEK293 cells.

A "transduced cell" is a cell into which a transgene (e.g., isomerohydrolase sequence) has been introduced. Accordingly, a "transduced" cell means a genetic change in a cell following incorporation of an exogenous molecule, for example, a nucleic acid (e.g., a transgene) into the cell. A "transduced" also includes progeny thereof. The cell(s) can be propagated (cultured) and the introduced protein (e.g., isomerohydrolase protein) expressed, or vector, such as rAAV, produced by the cell. In the case of culture cells, nucleic acid sequences, such as a heterologous nucleic acid sequence, or plasmid or vector has been inserted into a chromosome can be maintained over the course of a plurality of cell passages.

A "cell line" refers to a population of cells capable of continuous or prolonged growth and division in vitro under appropriate culture conditions. Cell lines can, but need not be, clonal populations derived from a single progenitor cell. In cell lines, spontaneous or induced changes can occur in karyotype during storage or transfer of such clonal populations, as well as during prolonged passaging in tissue culture. Thus, progeny cells derived from the cell line may not be precisely identical to the ancestral cells or cultures. An exemplary cell line applicable to the invention activity methods is HEK293, such as HEK-LRAT cells.

An "expression control element" refers to nucleic acid sequence(s) that influence expression of an operably linked nucleic acid. Control elements, including expression control elements as set forth herein such as promoters and enhancers. rAAV vectors can include one or more "expression control elements." Typically, such elements are included to facilitate proper heterologous polynucleotide transcription and if appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of rAAV vectors, expression control elements will typically be within 1 to 1000 nucleotides from the transcribed nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence. A promoter typically increases an amount expressed from operably linked nucleic acid as compared to an amount expressed when no promoter exists.

An "enhancer" as used herein can refer to a sequence that is located adjacent to the nucleic acid sequence, such as selectable marker, or heterologous nucleic acid sequence Enhancer elements are typically located upstream of a promoter element but also function and can be located downstream of or within a sequence. Hence, an enhancer element can be located upstream or downstream, e.g., within 100 base pairs, 200 base pairs, or 300 or more base pairs of the as selectable marker, and/or a heterologous nucleic acid encoding a therapeutic protein or polynucleotide sequence.

Enhancer elements typically increase expression of an operably linked nucleic acid above expression afforded by a promoter element.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g. promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for vector packaging into a rAAV particle. In various embodiments, a filler/stuffer nucleic acid sequence is an untranslated (non-protein encoding) segment of nucleic acid. For a nucleic acid sequence less than 4.7 Kb, the filler or stuffer polynucleotide sequence has a length that when combined (e.g., inserted into a vector) with the sequence has a total length between about 3.0-5.5 Kb, or between about 4.0-5.0 Kb, or between about 4.3-4.8 Kb.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., isomerohydrolase sequences, vectors, rAAV vectors, etc.) are an example of a genus of equivalent or similar features.

As used herein, the singular forms "a", "and," and "the" include plural referents unless the context clearly indicates otherwise. Thus, for example, reference to "an AAV vector," or "AAV particle," includes a plurality of such AAV vectors and AAV particles, and reference to "a cell" or "host cell" includes a plurality of cells and host cells.

The term "about" as used herein means values that are within 10% (plus or minus) of a reference value.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges are inclusive. Further, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

Protocol Summary

A protocol has been developed for the cell culture of Human Embryonic Kidney 293 cells with Lecithin Retinol Acyltransferase (HEK-LRAT) along with the corresponding viral transduction of RPE65 (AAV2-hRPE65v2) into the HEK-LRAT cells. This protocol is followed by the subsequent use of protein obtained from the cell transductions in an isomerase/isomerohydrolase activity assay.

HEK-LRAT cells are grown in culture before being plated and allowed to grow for 3 days prior to transduction. On the day of transduction, one well of cells is counted to determine cell count. The virus requirements for the transduction are calculated based on the cell count and desired MOI. After transduction, the cells are incubated for 1-3 days before the cells are harvested for analysis. Once the cells are harvested, pellets are homogenized in 100 μl in reaction buffer (10 mM BTP, pH 8.0 adjusted with 10N HCl, 100 mM NaCl) and the protein concentration is ascertained by Bradford assay. The volume of lysate needed to obtain 100 μg of total protein is calculated and the final volume is brought up to 200 μl by adding BTP (pH 8.0), NaCl, BSA, CRALBP and water so that the final concentrations of the components are 10 mM, 100 mM, 0.5%, and 25 μM, respectively. Protected from light from this point on, 24 of all-trans-retinol (prepared in 100% DMF) is added resulting in a final concentration of 5 μM and the samples are incubated at 37° C. for 2 hr. After 2 hr, the reaction is stopped (quenched) by adding 300410 mM BHT in Methanol and vortexing for 1 min. The samples are then extracted with hexane and analyzed.

Equipment and Materials

General Laboratory equipment and materials (equivalent equipment may be substituted).
  Rainin™ Certified Pipettes, Rainin™ Instruments, Woburn, MA
  Pipet-aid, Drummond
  Serological pipettes, individually wrapped, VWR
  Microbalance, Mettler AX205DR, Mettler Instruments
  pH meter, Orion, Thermo Scientific™
  FLUOstar OPTIMA, BMG Labtech™
  Forma 3100 incubator, Thermo Scientific™.
  Mini vortex mixer, VWR
  Waterbath, VWR
  Refrigerator, 2 to 8° C. Northland™
  Freezer, −35° C. to −20° C., Kenmore®
  Freezer, −80° C., Revco®
  Purifier Class II Biosafety Cabinet (BSC), Delta Series, Labconco
  Steri-Cycle $CO_2$ incubator, Thermo Scientific™
  Countess automated cell counter, Invitrogen
  Countess™ cell counting chamber slides, Invitrogen, or equivalent.
  Eppendorf® 5804R centrifuge
  Virsonic™ 100 sonicator
  Nikon® Eclipse TE300 microscope
  1.5 mL polypropylene microvials, VWR
  15 mL polypropylene tubes, VWR
  50 mL polypropylene tubes, VWR
  4 mL amber glass vials, VWR
  20 mL glass vials, VWR
  40 mL amber glass vials, VWR
  150 mL storage bottles, Corning™
  96-well plates, Thermo Scientific™
  Cell Scrapers, Fisher
  10 cm Nunclon cell culture dishes, Thermo Scientific™
  6 well plates, Fisher
  T150 CellBind flasks, Corning
  T75 CellBind flasks, Corning
  CellPort™ software, Absorption Systems
  $LN_2$ Cryotank, 2300 Series, Custom Biogenic Systems
  CryoElite 2 mL Cryogenic Vials, Wheaton
  2D Matrix Barcode Insert, Wheaton
  70% ethanol, VWR
  Trypan Blue stain 0.4%, Invitrogen
  Any Additional General Laboratory Equipment Reagents
  Note: A substitution of comparable grades of materials from different vendors is acceptable unless specifically stated.
  Human Embryonic Kidney 293 cells with Lecithin Retinol acyltransferase (HEK-LRAT)
  All-trans-Retinol, (from synthetic, ≥95% HPLC, crystalline), Cat #R7632, purchased from Sigma-Aldrich, MO;
  2, 6-Di-tert-butyl-4-methylphenol, (BHT, butylated hydroxytoluene), Cat #B1378-100G, Sigma-Aldrich, MO;
  N, N-Dimethylformamide, DMF, (HPLC grade, ≥99.9%), Cat #270547-1L, Sigma-Aldrich, MO;
  Methanol, MeOH, (UHPLC grade), Cat #A456-4, Fisher Scientific™, NJ;
  Water, $dH_2O$, in-house supply, Deionized and filtered (0.2 μm) using a Millipore system, Millipore Corp, Milford, MA;
  Dulbecco's Modified Eagle Medium, DMEM, high glucose, Cat #11965-092, Thermo Scientific™, MA;
  Penicillin-Streptomycin-Glutamine (100×), (Pen/Strep/L-Glut), Cat #10378-016, Thermo Scientific™, MA;
  Fetal Bovine Serum, certified, heat inactivated, US origin, Cat #10082-147, Thermo Scientific™, MA;
  Blasticidin® S HCl, 10 mg/ml, Cat #A11139-03, Thermo Scientific™, MA;
  0.25% Trypsin-EDTA, Cat #25200.056, Thermo Scientific™, MA;
  PBS (Dulbecco's Phosphate-Buffered Saline, 1×), Cat #14190-144, Thermo Scientific™ MA;
  EDTA (0.5M), Cat #15575-020, Thermo Scientific™, MA;
  37% Hydrochloric acid fuming (HCl), Cat #1003171000, Millipore;
  BTP (1,3-Bis [tris (hydroxymethyl) methylamino] propane), Cat #: B6755-100G, Sigma;
  NaCl, Cat #0241-2.5 KG, Amresco;
  BSA (Albumin, Bovine Serum), Cat #126579-100GM, Millipore;
  Thermo Scientific™ Pierce™ Coomassie (Bradford) Protein Assay, Cat #23200, Thermo Scientific™;
  Human CRALBP full length protein, EyeCRO™.
  Recombinant protein of human retinal pigment epithelium-specific protein 65 kDa (RPE65), Cat #TP310433, Origene™;

Preparation of Reagents
  Notes: The weighed amounts and/or solution volumes may be scaled up or down according to the needs.
  10 mM BHT in MeOH
  40 uM all-trans-Retinol in DMF
100 mM BTP, 10× Stock Solution, pH 8.0
  Weigh approximately 282.34 mg of BTP (Bis-Tris Propane™, M.W. 282.33) and dissolve in approximately 9.5 mL of $dH_2O$. Adjust to pH 8.0 with HCl then bring final volume to 10 mL with $dH_2O$. Store at 4° C. Expires in 1 month.
1M NaCl, 10× Stock Solution
  Weigh approximately 584.4 mg of NaCl (Sodium Chloride, M.W. 58.44) and dissolve in approximately 10 mL of $dH_2O$. Store at 4° C. Expires in 1 month.
5% BSA, 10× Stock
  Weigh approximately 100.0 mg of BSA and dissolve in approximately 2 mL of $dH_2O$. Store at 4° C. Expires in 3 days.

BTP-NaCl Reaction Buffer, 1× Solution

Combine 1 mL of 10×BTP with 1 mL 10× NaCl and 8 mL $dH_2O$. Mix well. Store at 4° C. Expires in 1 month.

DMEM Complete

In a Biosafety™ cabinet using aseptic technique, add 56.2 mL HI FBS and 5.6 mL Pen/Strep/L-Glut to 500 ml bottle of DMEM. Invert the bottle to mix. Add to CellPort™ software during preparation. Expires in 2 weeks.

DMEM Complete with Blasticidin®

In a Biosafety™ cabinet using aseptic technique, add 0.56 mL Blasticidin® to a full bottle of DMEM complete (or add Blasticidin® at 1:1000 to DMEM complete). Invert the bottle to mix. Add to CellPort software during preparation. Expires in 2 weeks.

DPBS with EDTA

In a Biosafety cabinet using aseptic technique, add 2.5 mL 0.5M EDTA to a full bottle of dPBS. Invert the bottle to mix. Add to CellPort™ software during preparation. Expires in 1 month.

Cell Culture

1) All cell culture should be handled with aseptic technique.
2) Documentation: The reagents and activities are recorded in the validated cell culture software with appropriate barcodes generated. In a rare instance of software inaccessibility, record data in a laboratory notebook until entry in the software.
3) Pre-warm all reagents (complete growth medium, trypsin-EDTA, DPBS with EDTA) in the 37° C. water bath.
4) Wipe down the inside of the biological safety cabinet with 70% ethanol. Place all materials that are not sensitive to UV light inside the cabinet and turn on the UV light for a minimum of 30 minutes before starting cell culture.
5) For thawing, select vial and remove it from Manufacturing Cryotank™ using the CellPort™ software before thawing.
6) Remove one vial from cryotank and thaw at 37° C. in water bath, spray vial with EtOH before placing in hood.
7) Transfer cells (1 mL at 1.0×10E6 cells/mL) from vial to a 15 mL tube with 9 mL DMEM complete.
8) Gently mix cells by pipetting and dispensing 5 to 10 times.

Centrifuge cells at 1200RPM for 5 min at room temperature, aspirate, and resuspend in 10 mL DMEM complete.

9) Cells seeded into 1 Corning™ Cellbind T75 with 10 mL of extra DMEM complete (for 20 mL total medium).
10) Place the flask in the incubator at 37° C. and 5% CO2.
11) Passaging:
   a. Pre-warm all reagents (complete growth medium, trypsin-EDTA, DPBS with EDTA) in the 37° C. water bath.
   b. Wipe down the inside of the biological safety cabinet with 70% ethanol. Place all materials that are not sensitive to UV light inside the cabinet and turn on the UV light for a minimum of 30 minutes before starting cell culture.
   c. Aspirate the medium from the culture flask.
   d. Wash cells with DPBS with EDTA once or twice depending on cell type. Aspirate the DPBS with EDTA from the culture flask.
   e. Add sufficient volume of Trypsin™ (0.25%, w/v)-EDTA (1 mM) solution to wet the surface of the monolayer (1 mL for a T75 and 2 mL for a T150).
   f. Incubate the flask at room temperature until cells start to detach.
   g. When the cells are starting to detach, tap the flask gently by hand to ensure complete detachment. Immediately add fresh medium to inactivate the protease reaction. Gently pipette up and down 5 to 10 times to ensure complete inactivation and to dissociate cell clumps.
   h. Remove an aliquot of cells, count the cells with a Countess™ automated cell counter.
   i. Inoculate a flask with the desired split ratio or cell density (seed T150 flasks at 5.0×10E5).
   j. Add a sufficient volume of complete growth medium to the flask(s) per the table below:

TABLE 1

Volume medium per flask.

| Flask Size | Total volume in flask (mL) |
|---|---|
| T-25 | 5-10 |
| T-75 | 18-20 |
| T-150 | 25-30 |
| T-175 | 30-35 |
| T-225 | 35-40 | k. Place the flask in the incubator at 37° C. and 5% CO2.
   l. Label flask(s) with the barcode from the validated cell culture software or cell line, passage number, date, and your initials in the rare instance the software is not accessible. After 1 passage post thaw, DMEM complete with Blasticidin is used for culture from this point on.

Cell Transduction

1) All cell culture should be handled with aseptic technique.
2) Documentation: The reagents and activities are recorded in the validated cell culture software with appropriate barcodes generated. In a rare instance of software inaccessibility, record data in a laboratory notebook until entry in the software
3) Cells dissociated and counted following steps in sections 12 a-h.
4) Cells seeded for transduction onto 6 well plates at 1.0×10E6 cells/well (6 well plates, Corning Vender #353046, Fisher Cat #08-772-1B) or 100 mm plates at 1.0×10E6 cells/plate (100 mm plates, Nunclon Surface, Vender #150350, Fisher Cat #12565020). Plate enough wells/plates for all transductions plus 1 for counting.
5) Transductions are performed 1 day after seeding.
6) On day of transduction, warm media, trypsin, and dPBS+EDTA.
7) From eQCM, open the Transduction template appropriate for plate type being used (templates in process of being added to eQCM) to use for calculations.
8) Aspirate media from well to be counted.
9) Add 0.5 mL trypsin to well, incubate 1-2 min until cells are released, then add 4.5 mL of dPBS for counting. For a 100 mm dish, add 2 mL trypsin to plate, incubate 1-2 min until cells are released, then add 8 mL of dPBS for counting.
10) Transfer all of the solution to a 15 mL tube and vortex to assure dissociation.
11) Remove 10 μL and add to 10 μL Trypan Blue, perform count.

Example

| cells/mL | volume (mL) | total cells |
|---|---|---|
| 1.7E+05 | 5 | 8.5E+05 |

12) Viral Process: Transducing 30 wells with 9 MOIs and 2 vectors=3 wells/MOI. Number of transductions and MOIs may vary until optimized.

TABLE 2

Example list of conditions and nomenclature for transduction.

| Condition | MOI | Nomenclature | Treatment (Tx) |
|---|---|---|---|
| Condition 1 | MOI 1.0E4 | Date-RS-1A, Date-RS-1B, Date-RS-1C Date-TA-1A, Date-TA-1B, Date-TA-1C | Tx at 10,000 vg/cell |
| Condition 2 | MOI 2.0E4 | Date-RS-2A, Date-RS-2B, Date-RS-2C Date-TA-2A, Date-TA-2B, Date-TA-2C | Tx at 20,000 vg/cell |
| Condition 3 | MOI 4.0E4 | Date-RS-3A, Date-RS-3B, Date-RS-3C Date-TA-3A, Date-TA-3B, Date-TA-3C | Tx at 40,000 vg/cell |
| Condition 4 | MOI 6.0E4 | Date-RS-4A, Date-RS-4B, Date-RS-4C Date-TA-4A, Date-TA-4B, Date-TA-4C | Tx at 60,000 vg/cell |
| Condition 5 | MOI 8.0E4 | Date-RS-5A, Date-RS-5B, Date-RS-5C Date-TA-5A, Date-TA-5B, Date-TA-5C | Tx at 80,000 vg/cell |
| Condition 6 | MOI 1.6E5 | Date-RS-6A, Date-RS-6B, Date-RS-6C Date-TA-6A, Date-TA-6B, Date-TA-6C | Tx at 160,000 vg/cell |
| Condition 7 | MOI 3.2E5 | Date-RS-7A, Date-RS-7B, Date-RS-7C Date-TA-7A, Date-TA-7B, Date-TA-7C | Tx at 320,000 vg/cell |
| Condition 8 | MOI 6.4E5 | Date-RS-8A, Date-RS-8B, Date-RS-8C Date-TA-8A, Date-TA-8B, Date-TA-8C | Tx at 640,000 vg/cell |
| Condition 9 | MOI 1.28E6 | Date-RS-9A, Date-RS-9B, Date-RS-9C Date-TA-9A, Date-TA-9B, Date-TA-9C | Tx at 1,280,000 vg/cell |
| Condition 10 | Formulation Buffer | Date- 10 (3 wells pooled) | Recovery QCs for LCMS Analysis |
| Condition 11 | NTC | Date- 11 (2 wells pooled) | Negative Control |

13) Based on the cell count, the volume of AAV treatment can be calculated:

TABLE 3

Example of volume of treated medium needed per condition based on Example in Table 2

| Condition | MOI | Number of Wells | Volume AAV Media Required (mL) | Add 5% of Media (mL) | Final Volume AAV Media Required (mL) |
|---|---|---|---|---|---|
| Condition 1 | MOI 1.0E4 | 3 | 6 | 0.3 | 6.3 |
| Condition 2 | MOI 2.0E1 | 3 | 6 | 0.3 | 6.3 |
| Condition 3 | MOI 4.0E4 | 3 | 6 | 0.3 | 6.3 |
| Condition 4 | MOI 6.0E4 | 3 | 6 | 0.3 | 6.3 |
| Condition 5 | MOI 8.0E4 | 3 | 6 | 0.3 | 6.3 |
| Condition 6 | MOI 1.6E5 | 3 | 6 | 0.3 | 6.3 |
| Condition 7 | MOI 3.2E5 | 3 | 6 | 0.3 | 6.3 |
| Condition 8 | MOI 6.4E5 | 3 | 6 | 0.3 | 6.3 |
| Condition 9 | MOI 1.28E6 | 3 | 6 | 0.3 | 6.3 |

TABLE 4

Example Calculations for Conditions in Table 3

| Condition | Counted Cells per Well | Vector Genomes Required Per Well | # of Wells | Total vg Required | Vector Lot # | Titer (vg/mL) | Volume AAV required (mL)* | Volume AAV required (µL) |
|---|---|---|---|---|---|---|---|---|
| Condition 1 | 8.50E+05 | 8.50E+09 | 3 | 2.55E+10 | RVC0164-2 | 3.50E+13 | 7.29E−04 | 0.729 |
| Condition 2 | 8.50E+05 | 1.70E+10 | 3 | 5.10E+10 | RVC0164-2 | 3.50E+13 | 1.46E−03 | 1.46 |
| Condition 3 | 8.50E+05 | 3.40E+10 | 3 | 1.02E+11 | RVC0164-2 | 3.50E+13 | 2.91E−03 | 2.91 |
| Condition 4 | 8.50E+05 | 5.10E+10 | 3 | 1.53E+11 | RVC0164-2 | 3.50E+13 | 4.37E−03 | 4.37 |

TABLE 4-continued

Example Calculations for Conditions in Table 3

| Condition | Counted Cells per Well | Vector Genomes Required Per Well | # of Wells | Total vg Required | Vector Lot # | Titer (vg/mL) | Volume AAV required (mL)* | Volume AAV required (µL) |
|---|---|---|---|---|---|---|---|---|
| Condition 5 | 8.50E+05 | 6.80E+10 | 3 | 2.04E+11 | RVC0164-2 | 3.50E+13 | 5.83E−03 | 5.83 |
| Condition 6 | 8.50E+05 | 1.36E+11 | 3 | 4.08E+11 | RVC0164-2 | 3.50E+13 | 1.17E−02 | 11.7 |
| Condition 7 | 8.50E+05 | 2.72E+11 | 3 | 8.16E+11 | RVC0164-2 | 3.50E+13 | 2.33E−02 | 23.3 |
| Condition 8 | 8.50E+05 | 5.44E+11 | 3 | 1.63E+12 | RVC0164-2 | 3.50E+13 | 4.66E−02 | 46.6 |
| Condition 9 | 8.50E+05 | 1.09E+12 | 3 | 3.26E+12 | RVC0164-2 | 3.50E+13 | 9.33E−02 | 93.3 |

*vg required divided by titer

14) Label 15 or 50 mL tubes with the appropriate nomenclature as shown in Table 2.
15) Create appropriate volume of AAV treated media to accommodate all conditions plus ~5% following formats in Tables 3 and 4.
16) Gently, add 2 mL of the appropriate treatment to each of the labeled wells. Add plain complete medium to 3 wells for NTC plates. 10 mL of medium is used in 100 mm dishes.
17) Incubate plates for 2.5 to 3 days.
18) Before harvesting the cells, take pictures on a microscope to show cell viability after transduction.
19) Cell pellet is harvested by power washing with a 1 mL pipette until all cells have dissociated from the plate, transferred to a 15 mL tube, and spun down (1200 RPM for ~5 min), medium is aspirated and cell pellets are frozen at −80° C. until use.

Protein Concentration Determination

1) Cell pellets are resuspended (if frozen they are thawed by resuspending) in 100 µL of 1×BTP-NaCl reaction buffer and transferred to a 1.5 mL tube.
2) Lysates are then taken to the sonicator. Set the sonicator between levels 10 and 11 and on remote control. The probe is rinsed with water before and after each sample is sonicated. The sonicator probe is placed in the sample and the button on the handle of the probe is pressed twice to quickly pulse 2 times.
3) Prepare 1:5 and 1:10 dilutions of each of the samples in 1×BTP-NaCl reaction buffer.
4) Prepare the diluted albumin (BSA) standards according to manufacturer's instructions (Thermo Scientific™ Pierce™ Coomassie (Bradford) Protein Assay, Cat #23200).
5) Following manufacturer's instructions, pipette 5 µL of each standard and unknown sample dilution in a 96 well plate. Run all in duplicate.
6) Add 250 µL of the Coomassie Reagent (warmed to room temperature; make 40 mL aliquots in 40 mL amber vials to avoid repeated warming of the reagent and only warm aliquots to room temperature 3 times before making a new aliquot) to each well.
7) Incubate the plate for 10 minutes at room temperature.
8) Measure the absorbance at or near 595 nm with the FLUOstar OPTIMA, use the method under absorbance for Bradford ZM.
   a. Open OPTIMA-control program→click test setup at the top of the program→click test protocol→select Absorbance on the left and select method BRADFORD_ZM→click edit→select layout and adjust the layout of the plate according to how the samples were loaded→click ok to save changes.
   b. Select measure at the top of the program→select method BRADFORD_ZM→click on the Plate IDs tab and fill in the IDS (ID1: project name, ID2: initials, ID3: date)→click Start Measurement to read the plate.
9) Save the run and open the OPTIMA MARS data analysis software. Click the OPEN file→select the file for the run based on the IDs and double click to open→click on the box next to Raw Data to show the raw data results in the plate grid→click on the box with the Excel spreadsheet 'X' symbol and the file will open in Excel→save the file and immediately upload it to eQCM.
10) Data analysis:
    a. From eQCM, open the raw data file and the Bradford analysis template (template in process of being added to eQCM).

TABLE 5

Example from template for calculating Bradford Standard.

| Vial | Duplicate 1 (units) | Duplicate 2 (units) | Duplicate 1 Normalized (units) | Duplicate 2 Normalized (units) | Average (units) | Final BSA Concentration (µg/ml) |
|---|---|---|---|---|---|---|
| A | 1.666 | 1.425 | 1.177 | 0.936 | 1.056 | 2000 |
| B | 1.323 | 1.342 | 0.834 | 0.853 | 0.843 | 1500 |
| C | 1.15 | 1.138 | 0.661 | 0.649 | 0.655 | 1000 |
| D | 0.983 | 1.054 | 0.494 | 0.565 | 0.529 | 750 |
| E | 0.852 | 0.831 | 0.363 | 0.342 | 0.352 | 500 |
| F | 0.722 | 0.715 | 0.233 | 0.226 | 0.229 | 250 |
| G | 0.602 | 0.585 | 0.113 | 0.096 | 0.104 | 125 |
| H | 0.533 | 0.523 | 0.044 | 0.034 | 0.039 | 25 |
| I (Blank) | 0.494 | 0.485 | | | | |
| I (Blank) Average | | 0.490 | | | | | b. Copy the raw values for the standards and paste value them into the top table on the 'Bradford Titration' tab (see Table 5) so they line up next to the column with Vials A-H. Since they are run in duplicate, there is a column for 'duplicate 1 and duplicate 2'.
c. Copy and paste value the raw values for the blank (standard vial I) and paste it into the cells next to 'Blank' in the table.
d. The 'Blank Average' will automatically be calculated as well as the 'duplicate 1 and 2 normalized' values and the 'Average' values.
e. Copy the calculated average values and paste them in the 'Instrument Readings' column to the right of the 'Standard values' on the tab labeled 'Standard Curve'. This will automatically calculate the standard curve.
f. Go back to the 'Bradford Titration' tab and copy and paste the raw data for the unknowns into the bottom table (see Table 6) for 'duplicate 1 and duplicate 2'. The 'duplicate 1 and 2 normalized values' and the 'Average values' will automatically be calculated. The sample names will need to be changed per assay.

TABLE 6

Example from template for calculating protein concentration of unknowns.

| Sample | Duplicate 1 (units) | Duplicate 2 (units) | Duplicate 1 Normalized (units) | Duplicate 2 Normalized (units) | Average (units) | Final BSA Conc. (µg/mL) | Dilution Factor | Non-Diluted BSA Concentration |
|---|---|---|---|---|---|---|---|---|
| 09-20-16-1A | 0.884 | 0.918 | 0.395 | 0.429 | 0.412 | 576.70 | 10.00 | 5 |
| 09-20-16-1B | 0.86 | 0.873 | 0.371 | 0.384 | 0.377 | 519.91 | 10.00 | 5 |
| 09-20-16-1C | 0.927 | 0.915 | 0.438 | 0.426 | 0.432 | 610.17 | 10.00 | 6 |
| 09-20-16-1D | 0.894 | 0.903 | 0.405 | 0.414 | 0.409 | 572.55 | 10.00 | 5 |
| 09-20-16-1E | 0.897 | 0.919 | 0.408 | 0.430 | 0.419 | 588.37 | 10.00 | 5 |
| 09-20-16-1F | 0.863 | 0.872 | 0.374 | 0.383 | 0.378 | 521.54 | 10.00 | 5 | g. Copy the calculated average values and paste them in the 'Reading of Unknown' column to the right of the standard curve on the tab labeled 'Standard Curve'. This will automatically calculate the 'Calculated Concentration'.
h. Copy the 'Calculated Concentrations' and paste value the results into the 'Final BSA Concentration' column of the bottom table (Table 6) on the 'Bradford Titration tab'. Add dilution factors into the appropriate column and the 'Non-diluted Concentrations' will automatically be calculated.
i. 'Save As' the file to an easy to locate place and name it with the date of analysis, Bradford analysis, and project information. Immediately upload the file to eQCM.
j. Add Bradford results to the Bradford Index and the protein use record for future use.
k. Return the samples to −80° C. until use in the assay.

Assay Sample Preparation
1) From eQCM, open the 'Assay protocol template' (template in process of being added to eQCM) and the Bradford results.
a. Copy and paste the sample IDs and the corresponding protein concentrations into the top table of the 'Protocol' tab (Table 7) and the 'Protein Volume' will automatically be calculated. Add the date of harvest in the 'Samples reception date'.

TABLE 7

Example from template for calculating volume of protein needed for activity assay.

| Source | Sample ID | Stock Protein Concentration (µg/µL) | Quantity Needed (µg) | Total Volume (µL) | Final Protein Concentration (µg/µL) | Protein Volume (µL) | Sample Reception Date |
|---|---|---|---|---|---|---|---|
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | |
| ASLP | | | 100 | 200 | 0.5 | | | b. Copy and paste the sample IDs into the corresponding cells in Table 8 on the 'Protocol' tab. Copy and paste the calculated 'Protein Volume' from Table 7 into the corresponding cells in the 'Total μL Protein (100 μg)' column of Table 8. The 'Volume of H2O' will automatically be calculated.

TABLE 8

Example of reaction setup for assay. Number of replicates may vary between assays.

| Tube # | Sample ID | Total μL Protein (100 μg) | Volume of H2O (μL) | Volume of BSA 10x (μL) | Volume of BTP Reaction Buffer 10x (μL) | Volume of NaCl 10x (μL) | Total Volume (μL) | CRALBP* (180 μg-25 μM)(μL) |
|---|---|---|---|---|---|---|---|---|
| | | | | 20 | 20 | 20 | 200 | |
| | | | | 20 | 20 | 20 | 200 | |
| | | | | 20 | 20 | 20 | 200 | |
| | | | | 20 | 20 | 20 | 200 | |
| | | | | 20 | 20 | 20 | 200 | |
| | | | | 20 | 20 | 20 | 200 | |
| | | | | 20 | 20 | 20 | 200 | |
| | | | | 20 | 20 | 20 | 200 | | c. Add the concentration of the CRALBP being used in the assay to the blacked bordered box below the second table and the 'CRALBP* (180 μg-25 μM)(4)' volumes will automatically be calculated in the table.

d. Add the notebooks numbers for the all-trans-retinol and 10 mM BHT in Methanol to the template for reference once they are received from the bioanalytical group.

e. 'Save As' the file to an easy to locate place and name it with the date, assay protocol, and project information. Immediately upload the file to eQCM. Print a copy to paste into a notebook to take to the lab.

2) Warm the reagents (10×BTP, 10×NaCl, and 10×BSA) up to room temperature.

3) Once the template is prepared, thaw the samples and the CRALBP needed for assay at room temperature. When the samples have thawed, re-sonicate them following the protocol in Section 7 Step 2.

4) Label the tubes according to the second table (Table 8) and add the reaction components in the following order: dH$_2$O, 10×BSA, 10×BTP, 10×NaCl, sample protein, and then the CRALBP following the second table (Table 8). Quickly vortex each component except for the protein before adding it to the tube. This can be completed in the light.

5) Everything from this point on MUST be done in the dark under dim yellow light.

a. Vortex the all-trans-retinol to ensure that it is well mixed before adding it to the samples. Carefully add 2 μL of the 500 μM all-trans-retinol in 100% DMF to each sample directly, being careful to watch for too much residue on the outside of the tip from the all-trans-retinol. Change tips between samples.

b. Once the all-trans-retinol has been added to all of the samples, quickly vortex all of the samples and place them in a 37° C. incubator for 2 hours (use of a black tube rack for the samples is ideal).

c. After 2 hours, the reaction is stopped by adding 300 μL 10 mM BHT in Methanol and the samples are vortexed for 1 min.

d. Place the samples in a box and ensure that they are well protected from light before analysis.

Example 2

Method Summary

An LC-MS/MS method has been developed for the analysis of 11-cis-retinol in the reaction matrix. Samples are prepared by using LLE (liquid-liquid extraction). A 200 μL aliquot of reaction matrix is mixed well with 300 μL of MeOH w/10 mM BHT (BHT: butylated hydroxytoluene), 20 μL of STD or QC working solutions, 20 μL of internal standard working solution (500 nM all-trans-retinol-d$_5$), and 300 μL of hexane. The sample is vortexed vigorously and centrifuged. The upper organic layer is carefully transferred to a clean 96-well plate, and evaporated to dryness under a gentle N$_2$ flow. The sample is reconstituted with 75 μL of Reconstitution Solution (MeOH w/10 mM BHT:water, 3:2 v/v). The analysis is performed using UPLC-MS/MS system by injecting 10 μL of the LLE-processed sample. All sample preparations are under dim yellow light.

The chromatography is performed on a Waters Acquity BEH C18, 1.7 μm, 2.1×100 mm column and analyzed by atmospheric pressure chemical ionization (APCI) mass spectrometry in the positive ion mode. An isocratic condition is used to elute the analytes using acetonitrile:methanol:isopropyl alcohol:water (45:20:5:30, v/v/v/v) as the mobile phase. With a flow rate of 0.35 mL/min, 11-cis-retinol elutes at approximately 8.8 minutes, all-trans-retinol at approximately 9.6 minutes, and the internal standard (all-trans-retinol-d$_5$) elutes at approximately 9.5 minutes. Total run time is approximately 11 minutes. The range of the assay is 1-25 nM for 11-cis-retinol while using a 200 μL reaction matrix sample volume.

Equipment

Column: Waters Acquity BEH C18, 1.7 μm, 2.1×100 mm (P/N: 186002352)

The LC-MS/MS System

Waters XEVO TQ-S mass spectrometer

Waters Acquity UPLC

General Laboratory Equipment (Equivalent Equipment May be Substituted)

Volumetric glassware, Class A

Rainin Certified Pipettes, Rainin Instruments, Woburn, Mass.

Microbalance, Mettler AX205DR, Mettler Instruments

Multi-Max vortex mixer

Thermolyne plate mixer

Refrigerator, 2 to 8° C. Revco

Freezer, −35° C. to −20° C., Revco

Freezer, −80° C.,

Beckman GS-6R centrifuge, or equivalent
Thermo Scientific Sorvaall T1 centrifuge, or equivalent
Evaporator, Zymark TurboVap 96, Zymark Corp., Hopkinton, MA
1.5 mL polypropylene microvials, VWR
Borosilicate glass tubes, 13×100 mm, VWR
15 mL polypropylene tubes, VWR
50 mL polypropylene tubes, VWR
4 mL amber glass vials, VWR
96-well, Deep Well plates, VWR
Any additional general laboratory equipment Instrument Conditions
LC Conditions
LC: Waters Acquity UPLC
Column: Waters Acquity BEH C18, 1.7 μm, 2.1×100 mm (P/N: 186002352)
Column Temperature: 40° C.
Mobile Phase A (MPA): acetonitrile: methanol: isopropyl alcohol:water (45:20:5:30, v/v/v/v)
Isocratic Program:

| Time (min) | Flow Rate (mL/min) | % A | % B |
|---|---|---|---|
| 0.0 | 0.35 | 100 | 0 |
| 11.0 | 0.35 | 100 | 0 |

Flow Rate: 350 μL/min
Run Time: ~11 minutes
Retention Times: 11-cis-retinol: ~8.8 min
  all-trans-retinol: ~9.6 min
  all-trans-retinol-$d_5$ (IS): ~9.5 min
Injection Volume: 10 μL
Autosampler Temperature: ~2-8° C.
Autosampler Wash #1: MeCN:IPA:$H_2O$:FA (3:3:3:0.1, v/v/v/v)
Autosampler Wash #2: 1% formic acid in water MS Conditions
Note: Mass spectrometer parameters may vary with different systems
Mass Spectrometer: Waters XEVO TQ-S
Source: APCI
Mode: Multiple Reaction Monitoring (MRM) with Positive Mode

| Compound | Precursor Ion | Product Ion | Dwell (s) | Cone (V) | CE (eV) |
|---|---|---|---|---|---|
| 11-cis-retinol or all-trans-retinol | 269.2 | 93.1 | 0.163 | 36 | 22 |
| all-trans-retinol-$d_5$ (IS) | 274.2 | 98.1 | 0.163 | 36 | 22 |

Instrument Settings:
Corona: 19 μA
Corona: 4 kV
Cone 12 V
Cone gas: 150 L/hr
Desolvation gas: 300 L/hr
Nebulizer gas: 4 Bar
Capillary voltage: 3.1 kV
Source Temperature: 150° C.
Proble Temperature: 500° C.
Collision gas: 0.15 mL/min
Note: cone and desolvation gases are $N_2$ while collision gas is argon.

Materials
Note: A substitution of comparable grades of materials from different vendors is acceptable unless specifically stated
11-cis-Retinol, pre-weighed, Cat #R252105, purchased from Toronto Research Chemicals, Canada;
All-trans-Retinol-$d_5$, Cat #R252002, purchased from Toronto Research Chemicals, Canada
All-trans-Retinol, (from synthetic, 95 HPLC, crystalline), Cat #R7632, purchased from Sigma-Aldrich, MO;
2, 6-Di-tert-butyl-4-methylphenol, (BHT, butylated hydroxytoluene), Cat #B1378-100G, Sigma-Aldrich, MO;
N, N-Dimethylformamide, DMF, (HPLC grade, 99.9%), Cat #270547-1L, Sigma-Aldrich, MO;
Hexane, (HPLC grade, 98.5%), Cat #293253-2L, Sigma-Aldrich, MO;
Acetonitrile, MeCN or ACN, (UHPLC grade), Cat #A955-4, Fisher Scientific, NJ;
Methanol, MeOH, (UHPLC grade), Cat #A456-4, Fisher Scientific, NJ;
Isopropyl Alcohol, IPA, (HPLC grade), Cat #PX1838-1, EMD Millipore Co., MA;
Formic Acid, FA (88%) (GR, ACS grade), Cat #0128-01, J.T. Baker, PA;
Water, d$H_2O$, in-house supply, Deionized and filtered (0.2 μm) using a Millipore system, Millipore Corp, Milford, MA;
Blank Reaction Matrix, prepared by Biological Lab Preparation of Reagents
Notes: The weighed amounts and/or solution volumes may be scaled up or down according to the needs.
10 mM BHT in MeOH
Weigh approximately 89.04 mg of BHT (butylated hydroxytoluene, M.W.=220.36) and dissolve in approximately 40.4 mL of MeOH. Store at RT. Expires in 1 week.
Reconstitution Solution (MeOH w/10 mM BHT:Water, 3:2 v/v)
Combine 12 mL of 10 mM BHT in MeOH with 8 mL de-ionized water. Mix well. Store at RT. Use it in the same day.
Mobile Phase A (MPA) Acetonitrile: Methanol: Isopropyl Alcohol:Water (45:20:5:30, v/v/v/v)
Combine 450 mL of MeCN, 200 mL MeOH, 50 mL IPA, and 300 mL deionized water. Mix well. Store at room temperature. Expires in 1 month.
Autosampler Wash Solution #1: MeCN:IPA:$H_2O$:FA (3:3:3:0.1, v/v/v/v)
Combine 300 mL of MeCN, 300 mL IPA, 300 mL deionized water and 10 mL of formic acid. Mix well. Store at room temperature. Expires in 1 month.
Autosampler Wash Solution #2: 1% Formic Acid in Water (v/v)
Combine 10 mL of formic acid with 1000 mL de-ionized water. Mix well. Store at RT. Expires in 1 month.
11-cis-Retinol Stock Solution (2.5 mM)
Under dim yellow light, add 1.46 mL of DMF into the original amber vial containing pre-weighed 1.110 mg of 11-cis-Retinol (M.W.=286.45, purity 94.12%). Vortex and easily dissolved. Store at a −80° C. Expiry to be determined.
All-trans-Retinol Stock Solution (2.5 mM)
Under dim yellow light, weigh approximately 2.97 mg of all-trans-Retinol (M.W.=286.45, purity 99.4%) and dissolve in approximately 4.12 mL of DMF. Vortex and easily dissolved. Store at a −80° C. Expiry to be determined.

All-trans-Retinol-$d_5$ Stock Solution (1 mM)

Under dim yellow light, add 1.63 mL of DMF into the original amber vial containing 0.5 mg of all-trans-Retinol-$d_5$ (M.W.=291.48, purity 95%). Vortex and easily dissolved. Store at a −80° C. Expiry to be determined.

IS Working Solution: 500 nM all-trans-Retinol-$d_5$

Under dim yellow light, add 5.0 μL 1 mM all-trans-Retinol-$d_5$ in DMF in 10 mL of Reconstitution Solution. Mix well. Store at a −80° C. Expiry to be determined.

System Suitability Sample (Equivalent to Extracted Mid QC: Final 26.7 nM 11-cis-Retinol/133 nM all-trans-Retinol-$d_5$)

Under dim yellow light, in a 96 well plate, transfer 40 μL of QC-M working solution (100 nM 11-cis-Retinol in Reconstitution Solution), 40 μL of IS working solution (500 nM all-trans-Retinol-$d_5$), and 70 μL of Reconstitution Solution. Mix well.

Another option: extracted Mid QC sample may be used as the "System Suitability sample".

Dose Solutions for Isomerohydrolase Activity Assays

Notes: The solution volumes may be scaled up or down according to the needs.

All preparations are under dim yellow light.

100 μM all-trans-Retinol in DMF

In a 4-mL Amber vial, combine 160 μL 2.5 mM all-trans-Retinol in DMF with 3.84 mL of DMF. Mix well.

40 μM all-trans-Retinol in DMF

In a 4-mL Amber vial, combine 64 μL 2.5 mM all-trans-Retinol in DMF with 3.94 mL of DMF. Mix well.

20 μM all-trans-Retinol in DMF

In a 4-mL Amber vial, combine 2.00 mL of 40 μM all-trans-Retinol in DMF with 2.00 mL of DMF. Mix well.

10 μM all-trans-Retinol in DMF

In a 4-mL Amber vial, combine 2.00 mL of 20 μM all-trans-Retinol in DMF with 2.00 mL of DMF. Mix well.

30% DMF

Combine 6.0 mL of DMF with 14 mL de-ionized water. Mix well. Store at RT. Expires in 1 month.

40 μM all-trans-Retinol in 30% DMF

In a 4-mL Amber vial, combine 64 μL 2.5 mM all-trans-Retinol in DMF with 3.94 mL of 30% DMF. Mix well.

16 μM all-trans-Retinol in 30% DMF

In a 4-mL Amber vial, combine 1.00 mL of 40 μM all-trans-Retinol in with 1.50 mL of 30% DMF. Mix well.

8 μM all-trans-Retinol in 30% DMF

In a 4-mL Amber vial, combine 1.00 mL of 16 μM all-trans-Retinol in with 1.00 mL of 30% DMF. Mix well.

Validation Specific Reagents

Note: The solution volumes may be scaled up or down according to the needs.

Working Standard and QC Preparation

Notes: Volumes may be scaled according to needs.

All preparations are under dim yellow light.

Prepare a set of working solutions by serial dilutions using the schemes shown in the table below. All working solutions are prepared using Reconstitution Solution (MeOH w/10 mM BHT:water, 3:2 v/v) and stored at −80° C.

TABLE 9

Preparation of 11-cis-Retinol Standard and QC Working Solutions

| STD/QC | Source | Source Vol. (μL) | *Diluent Vol. (μL) | Total Vol. (μL) | Working Solution Conc. (nM) | Conc. in Matrix (nM) |
| --- | --- | --- | --- | --- | --- | --- |
| WS-INT1 | Stock (2.5 mM in DMF) | 80 | 920 μL DMF | 1000 | 200,000 | NA |
| WS-INT2 | WS-INT1 | 80 | 920 μL DMF | 1000 | 16,000 | NA |
| WS-INT3 | WS-INT2 | 60 | 900 μL | 960 | 1,000 | NA |
| WS 1 | WS-INT3 | 250 | 750 | 1000 | 250 | 25 |
| WS 2 | WS-INT3 | 200 | 800 | 1000 | 200 | 20 |
| WS 3 | WS-INT3 | 150 | 850 | 1000 | 150 | 15 |
| WS 4 | WS-INT3 | 100 | 900 | 1000 | 100 | 10 |
| WS 5 | WS-INT3 | 75 | 925 | 1000 | 75 | 7.5 |
| WS 6 | WS-INT3 | 50 | 950 | 1000 | 50 | 5 |
| WS 7 | WS 2 | 100 | 900 | 1000 | 20 | 2 |
| WS 8 | WS 4 | 100 | 900 | 1000 | 10 | 1 |
| QC-INT1 | Stock (2.5 mM in DMF) | 80 | 920 μL DMF | 1000 | 200,000 | NA |
| QC-INT2 | QC-INT1 | 80 | 920 μL DMF | 1000 | 16,000 | NA |
| QC-INT3 | QC-INT2 | 60 | 900 μL | 960 | 1,000 | NA |
| QC-H | QC-INT3 | 200 | 800 | 1000 | 200 | 20 |
| QC-M | QC-INT3 | 100 | 900 | 1000 | 100 | 10 |
| QC-L | QC-H | 100 | 900 | 1000 | 20 | 2 |
| QC-LL | QC-M | 100 | 900 | 1000 | 10 | 1 |

*Diluent = Reconstitution Solution = (MeOH w/5 mM BHT):$H_2O$, 3:2 v/v

System Suitability

System suitability is optional but recommended

Equilibrate the UPLC-MS/MS system for approximately 10 minutes.

Inject System Suitability samples (N=5).

Calculate RSD (%) for RT and peak area.

Sample Preparation

LLE for Standard/QC Samples (all Prep Under Dim Yellow Light):

1) Add 20 μL of working standard or QC solution into Eppendorf vials (1.5-mL). Add 20 μL of Reconstitution Solution to those "Blank" samples.

2) Pipette 200 μL of Reaction Matrix.

3) Pipette 300 μL of MeOH w/10 mM BHT, gently vortex ~3 seconds.
4) Add 20 μL ISWS (500 nM all-trans-retinol-$d_5$ in Reconstitution Solution).
5) Add 300 μL hexane into each sample vial.
6) Cover the cap and vortex vigorously for ~5 minutes, centrifuge at 13,000 rpm for ~5 minutes.
7) Carefully transfer (~250 μL) upper organic layer to a clean 96-well plate.
8) Evaporate the samples to dryness at 40° C. under a gentle $N_2$ flow by using the TurboVap (or equivalent). The samples should be dry in ~30 minutes. Start with a gas flow setting of ~25.
9) Add 75 μL of Reconstitution Solution and mix well. Centrifuge at 3,000 rpm for ~2 minutes.
10) Analyze using UPLC-MS/MS by injecting 10 μL of the sample.

LLE for Incurred Samples (all Prep Under Dim Yellow Light):
a) Add 20 μL of Reconstitution Solution, 20 μL ISWS (500 nM all-trans-retinol-$d_5$ in Reconstitution Solution), and 300 μL hexane into each sample vial (In 1.5-mL Eppendorf vial: 2-hour-incubated 200 μL reaction matrix sample was treated with 300 μL MeOH w/10 mM BHT to quench the reaction).
b) Then, follow above "standard/QC samples" preparation Steps 6 to 10.

Data Processing
  Process data using the Waters MassLynx V4.1 software. Calculations for the standards, QC and samples will be performed using peak area ratios to the internal standard. The analysis method will use a quadratic regression model with a $1/x^2$ weighting.

Acceptance Criteria
  Acceptance criteria for analytical batches are described below for validations and for sample analysis.

Example 3

Validation Summary
The isomerohydrolase activity assay qualification was performed as described above unless otherwise noted. The assay was qualified for testing both drug substance (DS) and drug product (DP) since both have the same formulation. The following parameters were evaluated:
  System Suitability and Sample Acceptance
  Specificity (Non-interference of Formulation Buffer)
  Dilutional Linearity
  Precision (Intermediate Precision)
  Relative Accuracy
  Range
All described studies concluded:
  The isomerohydrolase activity assay is specific, linear, accurate, and precise.
  System suitability criteria were met for each analytical set.
  The range of 50% to 150% of the nominal method concentrations, multiplicity of infection (MOI) 1.00E+04, 2.00E+04, 4.00E+04, 6.00E+04, 8.00E+04, 1.60E+05, 3.20E+05, 6.40E+05, 1.28E+06 AAV vector genomes (vg) per cell, is supported by the linearity, accuracy, and precision data.
The method was shown to be suitable for its intended purpose.

| Abbreviation | Description |
| --- | --- |
| AAV2-hRPE65v2 | Drug Substance or Drug Product Nomenclature |
| 11cROL | 11-cis-retinol |
| CI | Confidence Interval |
| CRALBP | Cellular Retinaldehyde Binding Protein |
| CV | Coefficient of Variation |
| DP | Drug Product |
| DS | Drug Substance |
| GCV | Geometric Coefficient of Variation |
| HEK | Human Embryonic Kidney |
| IP | Intermediate Precision |
| ln(RP) | natural log of the |
| relative potency LRAT | Lecithin Retinol |
| Acyltransferase MOI | Multiplicity of Infection |
| RS | Reference Standard |
| SOP | Standard Operating Procedure |
| SSQ | Sum of squares |
| STD | Reference Standard (PLA software) |
| TA | Test Article |
| UNK or UNK1 | Test Article (PLA software) |
| USP | United States Pharmacopeia |
| vg | Vector Genomes |

Analytical Reference Standard
Analytical Reference Standard Name: AAV2-hRPE65v2 Drug Substance
  Concentration: 4.86e12 vg/mL
Sample (Test Article)
Sample Name: AAV2-hRPE65v2 Drug Substance
  Concentration: 4.86e12 vg/mL
Cellular Retinaldehyde Binding Protein (CRALBP)
Sample Name: CRALBP
  3.8 mg/mL; Average 2.675 pmol 11cROL
  Or 4.0 mg/mL; Average 2.758 pmol 11cROL
  Supplier: EyeCRO/Oklahoma City, OK
HEK293-LRAT Cells
Sample Name: HEK293-LRAT Cells
AAV2-hRPE65v2 Formulation Buffer
  Formulation Buffer Composition: 10 mM sodium phosphate, 180 mM sodium chloride, 0.001% pluronic F68, pH 7.3.
Study Design, Results Summary and Recommendations for Validation
The results for system suitability and sample acceptance criteria were evaluated and reported. Results from invalid assays (where system suitability criteria were not met) were not used. Only results from passing assays were used for the evaluation of Specificity, Relative Accuracy, Precision, Range, and Dilutional Linearity. The Summary of Parameters, Results and Recommendations for Validation Acceptance Criteria are summarized in Table 10.

TABLE 10

Summary of Parameters, Results and Recommendations for Validation

| Parameter | Methodology | Qualification Protocol Acceptance Criteria | Results | Recommendations for Validation Acceptance Criteria |
|---|---|---|---|---|
| System Suitability and Sample Acceptance | | Report Results | System Suitability and Sample Acceptance criteria were met for each analytical set. | Evaluate results against the method system suitability criteria. Report results of system suitability and sample acceptance criteria. |
| Specificity Non-Interference | Non-Interference of Formulation Buffer, 9 MOI (Level 100%) | Report Results | No dose response observed for AAV2-hRPE65v2 formulation buffer. The sample slope criterion failed the method acceptance criteria. PLA v3.0 parallelism assessment was rejected due to lack of data fit. | When compared to the dose-response elicited by the standard, no dose-response is observed with the AAV2-hRPE65v2 formulation buffer. The AAV2-hRPE65v2 formulation buffer sample must fail the sample slope criterion. The AAV2-hRPE65v2 formulation buffer sample must fail the equivalence test: difference of slopes criteria in PLA. Alternatively, the PLA v3.0 parallelism assessment may be rejected due to lack of data to support the required analysis. |
| Dilutional Linearity | Linear curve (AAV2-hRPE65v2 Analytical Reference Standard) analysis of 9 MOI (1.00E+04, 2.00E+04, 4.00E+04, 6.00E+04, 8.00E+04, 1.60E+05, 3.20E+05, 6.40E+05, 1.28E+06) | Report Results | The coefficient of determination ($R^2$) was 0.91 | The coefficient of determination ($R^2$) must be ≥0.85 |
| Precision | Intermediate Precision Analyst-to-Analyst (Analyst 1 and Analyst 2) and Day-to-Day 1. One Preparation of Analytical Reference Standard 2. One Preparation of Test Article (Sample) 3. Both RS (100%) and TA (50%, 100%, or 150%) at 9 MOI per analyst per day. Analytical Reference Standard was used as the Test Article (Sample) | Report Results | 50%: % IP = 9.5% 100%: % IP = 9.9% 150%: % IP = 15.5% Pooled : % IP = 11.3% | The intermediate precision (IP) for each validation concentration level must be ≤30%. The pooled intermediate precision (IP) value from data generated at the three concentration levels must be ≤30% |
| Relative Accuracy | Analytical Reference Standard was used as the Test Article (Sample) and tested at three different concentrations. or three levels (50%, 100%, 150%), against Reference Standard prepared at 100% | Report Results | 50%: % Bias = −0.6% 100%: % Bias = +0.3% 150%: % Bias = +10.0% | The relative bias for each accuracy level must be −25% ≤ x ≤ +25%. |
| Range | Results from Precision, Dilutional Linearity, and Relative Accuracy | Report Results | 50% to 150% of the nominal method concentration | Report the range that is supported by the relative accuracy, intermediate precision, and dilutional linearity data |

1. Parameters that were not included in this qualification are: Precision (Repeatability), Forced Degradation, and Robustness.

System Suitability
Definition

System suitability testing is an integral part of many analytical procedures. The testing is based on the concept that the equipment, electronics, analytical operations and samples to be analyzed constitute an integral system that can be evaluated as such. System suitability test parameters to be established for a particular procedure depend on the type of procedure being qualified.

Experimental Design

System suitability and sample acceptance were performed for each analysis set as described above. All statistical analysis was performed by Tunnell Consulting (King of Prussia, PA) and data provided to Absorption Systems for inclusion in the report.

Acceptance Criteria

Results, Discussion and Conclusions

The assay acceptance and sample acceptance criteria where appropriate were met for each analysis set.

Two assays were repeated during the qualification, assay 6 and assay 2. Assay 6 (Intermediate Precision, Analyst 2, Day 1, 100%) did not meet the predefined acceptance criteria for outliers and failed the warning level for maximum number of outliers. The outliers were most likely due to lack of cell lysate homogeneity resulting in variable protein concentration measurements as described below.

In Assay 6, protein concentration was unusually low for sample 12-2-16-9RS-C. The one enzyme assay performed on sample 12-2-16-9RS-C generated an unusually high concentration of 11-cis-retinol (11cROL), indicating the low protein reading may have been inaccurate, causing more protein to be added to the enzyme activity assay than required. A similar observation was made for samples 12-02-16-6RS-A and 12-02-16-7RS-B in which unusually high protein concentrations resulted in unusually low 11cROL concentrations. These samples or data points were listed as technical outliers because cell lysate samples may not have been sufficiently mixed during the first sonication step before moving into the Bradford assay resulting in inaccurate protein readings and therefore inaccurate protein being added to the enzyme activity assay. Analyst 2 was retrained and Assay 6 was repeated. Repeat of Assay 6 met the assay acceptance and sample acceptance criteria.

During the investigation for Assay 6, it was decided to repeat Assay 2 as well. While Assay 2 (Intermediate Precision, Analyst 2, Day 1, 50%) did meet the assay system suitability and sample acceptance criteria, the data was very highly variable for the same reasons identified in Assay 6. Analyst 2 was retrained and Assay 2 was repeated. Repeat of Assay 2 met the assay acceptance and sample acceptance criteria.

Specificity

Definition

Specificity is the ability to assess unequivocally the test article (TA) response in the presence of components which may be expected to be present during sample analysis. Typically, these include impurities, degradants, and sample matrix.

Non-Interference of Formulation Buffer—Experimental Design

The specificity non-interference of the assay was evaluated by preparing and analyzing AAV2-hRPE65v2 Formulation Buffer. The Formulation Buffer was diluted using the same dilution volumes as the Reference Standard and treated similar to the TA for all 9 MOI (Level 100%).

Acceptance Criteria

Results, Discussion and Conclusions

Figure 8:
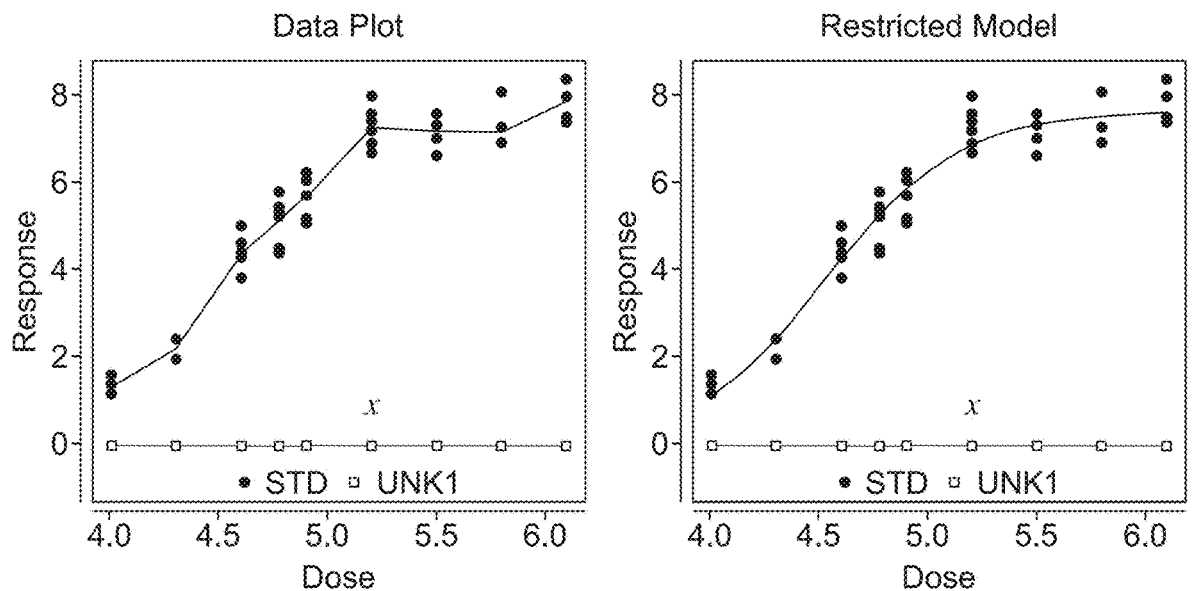
FIG. 8 shows PLA 3.0 Dose Response Curves for AAV2-hRPE65v2 Reference Standard (Dark) and Specificity Sample of Formulation Buffer (Light) from Assay 14.

A dose response curve for the formulation buffer is shown in FIG. 8. When compared to the dose-response elicited by the analytical reference standard, no dose-response was observed with the AAV2-hRPE65v2 formulation buffer. PLA v3.0 did provide an estimate of relative potency, essentially zero. The AAV2-hRPE65v2 formulation buffer sample failed the sample slope criterion. The PLA v3.0 parallelism assessment was rejected due to lack of data to support the required analysis. This concludes that the method is specific to AAV2-hRPE65v2.

Dilutional Linearity

Definition

The linearity of an analytical method proves the ability to obtain test results that are directly proportional to the concentration of the sample.

Experimental Design

Linearity was demonstrated over the range of the linear curve, using AAV2-hRPE65v2 analytical reference standard, at the following nine MOI; 1.00E+04, 2.00E+04, 4.00E+04, 6.00E+04, 8.00E+04, 1.60E+05, 3.20E+05, 6.40E+05, and 1.28E+06.

Acceptance Criteria

Results, Discussion and Conclusions

The acceptance criteria described were met. The coefficient of determination ($R^2$) was 0.91. Dilutional linearity of the assay is confirmed in FIG. 9 because the 95% confidence bound on the fitted line includes the line of identity. Linearity plot in FIG. 9 is generated from the values of the 13 assays in Table 11, and estimated relative potency values are plotted against their respective target potency values.

Table 11 provides the estimated relative potency reported by PLA v3.0 for each of the 13 assays with Target relative potency levels of either 0.5, 1.0 or 1.5. The natural log of relative potency ("ln(RP)") is also provided and used in Tables 16 and 17. Note that all the equations used in the calculations in Tables 11, 16, and 17 are given in USP<1033>. Assay 14 (discussed in Section 8.1 under Specificity) is not included in this statistical analysis here because the sample contained no AAV2-hRPE65v2 and as a result, as expected, the PLA v3.0 suitability tests could not be calculated for this assay data.

Figure 9:
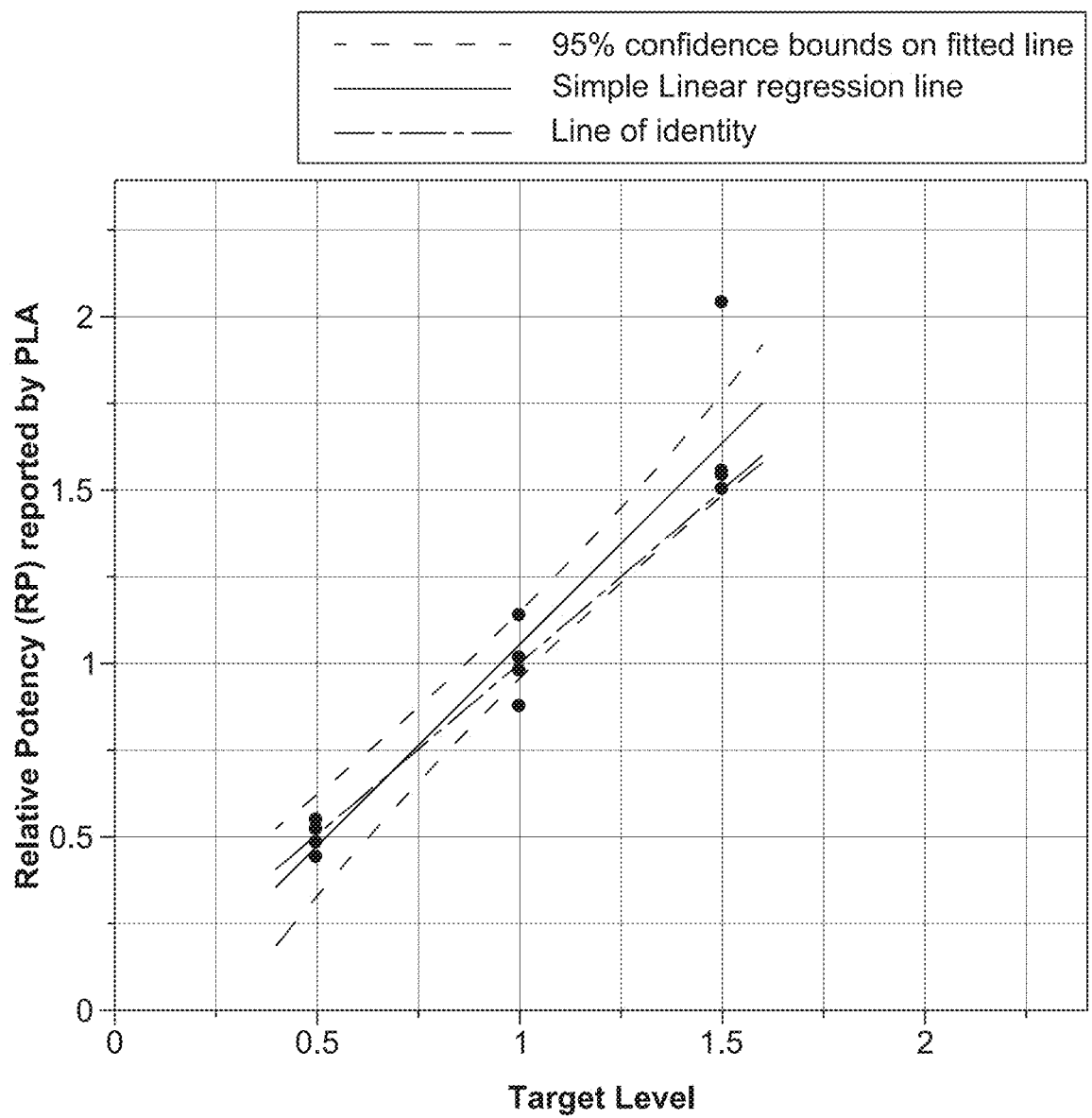
FIG. 9 shows Dilution Linearity: Symbols Represent Estimated Relative Potency Values from the 13 Assays Listed in Table 11 Plotted Against their Respective Target potency values. The fitted regression line is Relative Potency (RP) reported by PLA v3.0=−0.112815+1.1649975*Target Level.

Table 12 provides the 95% confidence interval estimates of the intercept and slope of the simple linear regression from FIG. 9. The "Target Level" Term in Table 12 refers to an estimate of the regression slope. The confidence interval (i.e. between lower 95%-upper 95% in Table 12) for the intercept includes 0 and the confidence interval for the slope includes 1, as expected for dilutional linearity. The p-value (Prob>|t|) for the slope represents a statistical test that the slope is equal to zero. The fact that the observed p-value is very low (<0.0001) is strong evidence that the slope is not zero.

Table 13 provides some additional statistical output associated with the fitted line in FIG. 9. The RSquare in particular indicates that 91.4% of the variance of the individual values in FIG. 9 is accounted for by the dilution linearity relationship.

TABLE 11

Estimated Relative Potency for Each of the 13 Qualification Assays with Non-zero Target Levels

| Assay | Analyst | Day | Target Level | Relative Potency (RP) reported by PLA v3.0 | ln(RP) |
|---|---|---|---|---|---|
| 1 | 1 | 1 | 0.5 | 0.48255 | −0.729 |
| 2-Repeat | 2 | 1 | 0.5 | 0.44382 | −0.812 |
| 3 | 1 | 2 | 0.5 | 0.52168 | −0.651 |
| 4 | 2 | 2 | 0.5 | 0.54563 | −0.606 |
| 5 | 1 | 1 | 1 | 0.97626 | −0.024 |
| 6-Repeat | 2 | 1 | 1 | 1.01627 | 0.016 |
| 7 | 1 | 2 | 1 | 1.14166 | 0.132 |
| 8 | 2 | 2 | 1 | 1.01849 | 0.018 |
| 13 | 1 | 3 | 1 | 0.87834 | −0.130 |
| 9 | 1 | 1 | 1.5 | 1.50490 | 0.409 |
| 10 | 2 | 1 | 1.5 | 1.55749 | 0.443 |
| 11 | 1 | 2 | 1.5 | 1.54618 | 0.436 |
| 12 | 2 | 2 | 1.5 | 2.04510 | 0.715 |

TABLE 12

Intercept and Slope ("Target Level") Estimates
from the Simple Linear Regression in FIG. 9
Parameter Estimates

| Term | Estimate | Std Error | t Ratio | Prob > |t| | Lower 95% | Upper 95% |
|---|---|---|---|---|---|---|
| Intercept | −0.112815 | 0.115601 | −0.98 | 0.3501 | −0.367252 | 0.1416214 |
| Target Level | 1.1649975 | 0.107619 | 10.83 | <0.0001* | 0.9281299 | 1.4018651 |

*The JMP regression output automatically flags any p-value <0.05 just to note statistical significance. It is expected to see statistical significance here so the number with * is acceptable. The "Target Level" line estimates the Slope. The value with * indicates that the slope is different from zero. The confidence interval, between the lower 95% and upper 95%, brackets 1.

TABLE 13

Summary Statistics from the Simple Linear Regression in FIG. 9

| | |
|---|---|
| RSquare | 0.914187 |
| RSquare Adj | 0.906385 |
| Root Mean Square Error | 0.152196 |
| Mean of Response | 1.052182 |
| Observations (or Sum Weights) | 13 |

Precision
Definition

Per ICH Guideline Q2 (R1), the precision of an analytical procedure expresses the closeness of agreement (degree of scatter) between a series of measurements obtained from multiple sampling of the same homogeneous sample under the prescribed conditions. The precision of an analytical procedure is usually expressed as the variance, standard deviation or coefficient of variation of a series of measurements.

Intermediate Precision—Definition

The intermediate precision expresses within laboratory variations of the analytical method: different days, different analysts, different equipment, etc.

Intermediate Precision—Experimental Design

The intermediate precision of the method was determined using a variance component analysis, as described in USP General Chapter <1033> Biological Assay Validation. AAV2-hRPE65v2 Analytical Reference Standard was used as the sample and tested at three different ranges of concentrations or three different sets of MOI levels: 50%, 100% and 150%.

The preparation of MOI dilutions were documented in the laboratory notebook, since volume of vector required depended on the cell count. The matrix for the MOI at three different levels is provided in Table 14.

TABLE 14

Summary of MOIs at 50%, 100%, and 150%

| MOI# | MOI 50% Range | MOI 100% Range | MOI 150% Range |
|---|---|---|---|
| 1 | 5.00E+03 | 1.00E+04 | 1.50E+04 |
| 2 | 1.00E+04 | 2.00E+04 | 3.00E+04 |
| 3 | 2.00E+04 | 4.00E+04 | 6.00E+04 |
| 4 | 3.00E+04 | 6.00E+04 | 9.00E+04 |
| 5 | 4.00E+04 | 8.00E+04 | 1.20E+05 |
| 6 | 8.00E+04 | 1.60E+05 | 2.40E+05 |
| 7 | 1.60E+05 | 3.20E+05 | 4.80E+05 |
| 8 | 3.20E+05 | 6.40E+05 | 9.60E+05 |
| 9 | 6.40E+05 | 1.28E+06 | 1.92E+06 |

Intermediate precision was determined from the results of the assays as performed by two different analysts, over two different days, and at the three different levels of accuracy: 50%, 100% and 150%. Analyst two, day three was included to support the third independent preparation required for intermediate precision.

Analyst 1 and Analyst 2 were two different analysts. Analyst 2 was not represented by multiple people.

One preparation of Analytical Reference Standard and one sample preparation of TA (Analytical Reference Standard was used as the sample or TA) was prepared per MOI per analyst per day of testing.

Analyst 1 (or Analyst 2), prepared both Analytical RS and TA at the following nine MOI for Level 100% (see FIG. 10): 1.00E+04, 2.00E+04, 4.00E+04, 6.00E+04, 8.00E+04, 1.60E+05, 3.20E+05, 6.40E+05, and 1.28E+06. The default plate map of the 50% and 150% MOI Levels, is provided in FIG. 11 and FIG. 12 respectively.

The matrix for determining intermediate precision is provided in Table 15.

TABLE 15

Intermediate Precision Summary of Experiments at Three
Different Accuracy Levels: 50%, 100% and 150%

| | | Analyst | | | | | | |
|---|---|---|---|---|---|---|---|---|
| | | 1 | | 2 | | 1 | 2 | 1 | 2 |
| | | Day | | | | | | | |
| | | 1 | 2 | 1 | 2 | 3[1] | 1 | 2 | 1 | 2 | 1 | 2 | 1 | 2 |
| MOI or | 50% | | | | | | X | X | X | X | | | | |
| Concentrations (%) | 100% | X | X | X | X | X | | | | | | | | |
| at 3 Accuracy Levels | 150% | | | | | | | | | | X | X | X | X |

[1]Analyst 2, Day 3 supports the third independent preparation required for intermediate precision.

X: Indicates which treatment was performed by a specific analyst on a specific day.

The methods as described above were performed for the sample and data analysis.
Acceptance Criteria
Results, Discussion and Conclusions The acceptance criteria were met. The intermediate precision (IP) for each qualification concentration target level relative potency of 0.5 (50%), 1.0 (100%), and 1.5 (150%) is 9.5%, 9.9%, and 15.5% respectively and is ≤30%. The pooled intermediate precision (IP) value, also referred as an overall estimation of % GCV, from data generated at the three concentration levels is 11.3% and is ≤30%. IP results are reported in Table 16 and Table 17.

Figure 13:
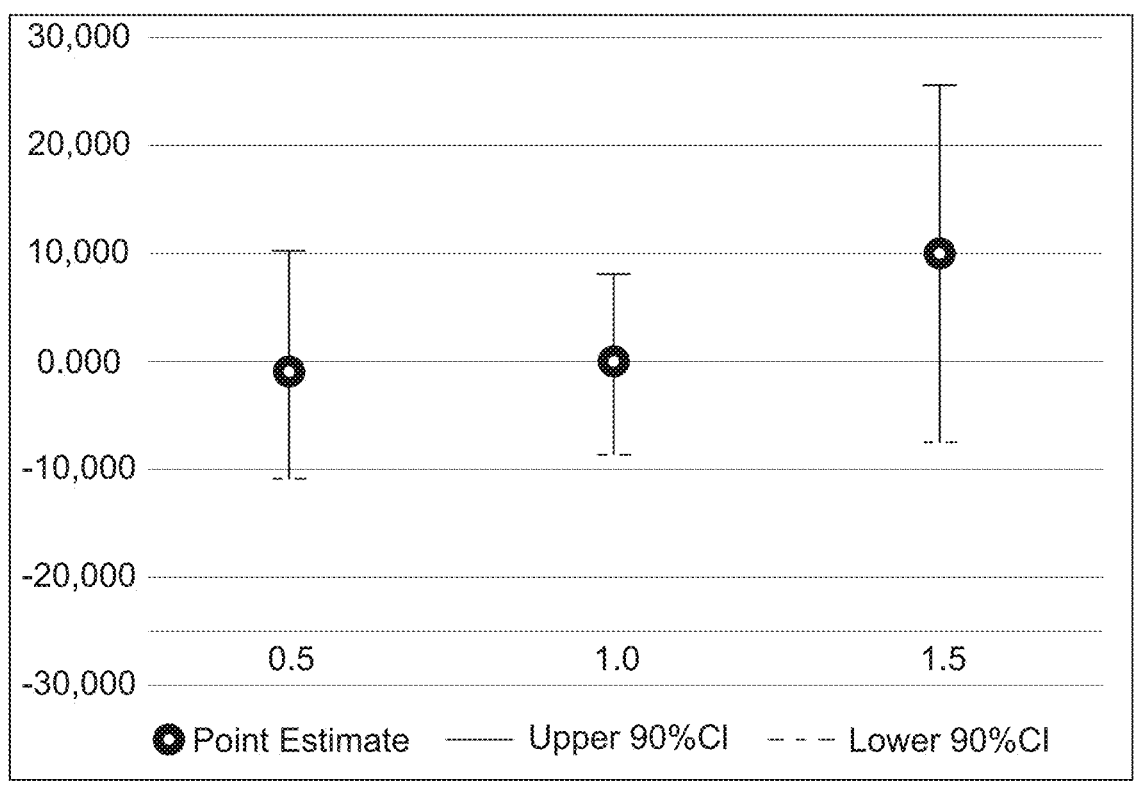
FIG. 13 shows Relative Bias (dot) and its 90% Confidence Interval Estimated for each Target Level from Table 11.
Figure 14:
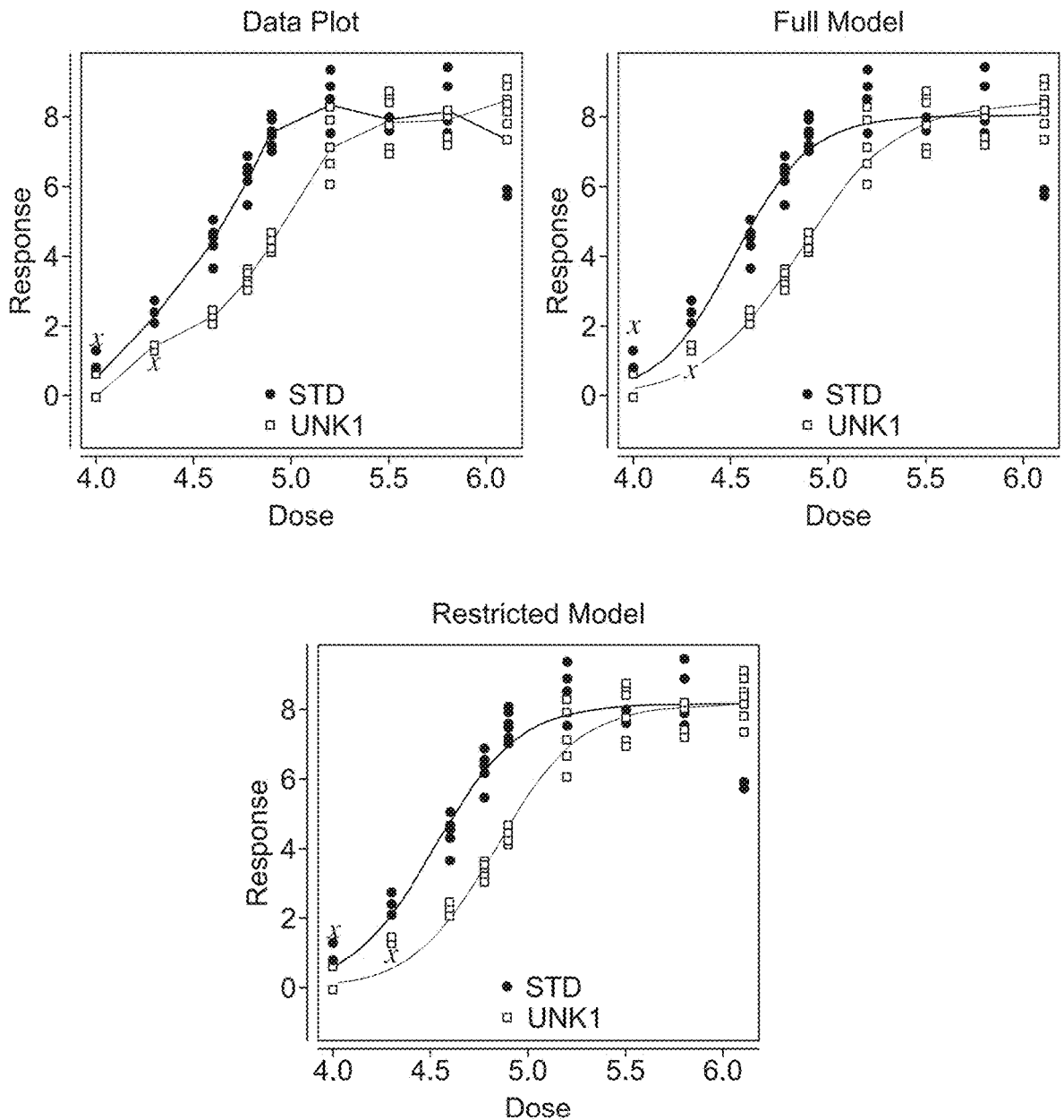
FIG. 14 shows PLA 3.0 Dose Response Curves for AAV2-hRPE65v2 Reference Standard (Dark) and Test Article Day 1, Analyst 1, 50% (Light) from Assay 1.
Figure 15:
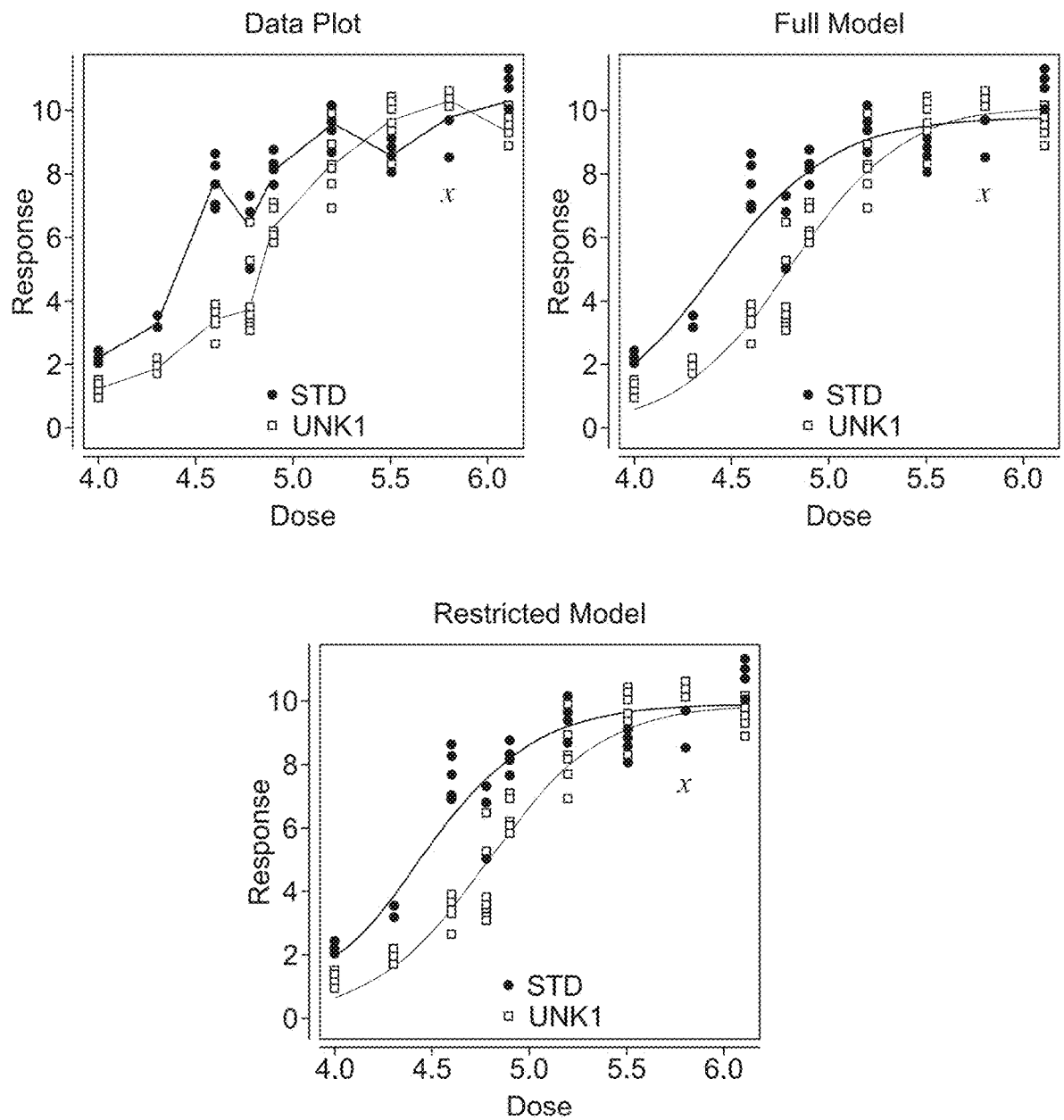
FIG. 15 shows PLA 3.0 Dose Response Curves for AAV2-hRPE65v2 Reference Standard (Dark) and Test Article Day 1, Analyst 2, 50% (Light) from Assay 2 Repeat.
Figure 16:
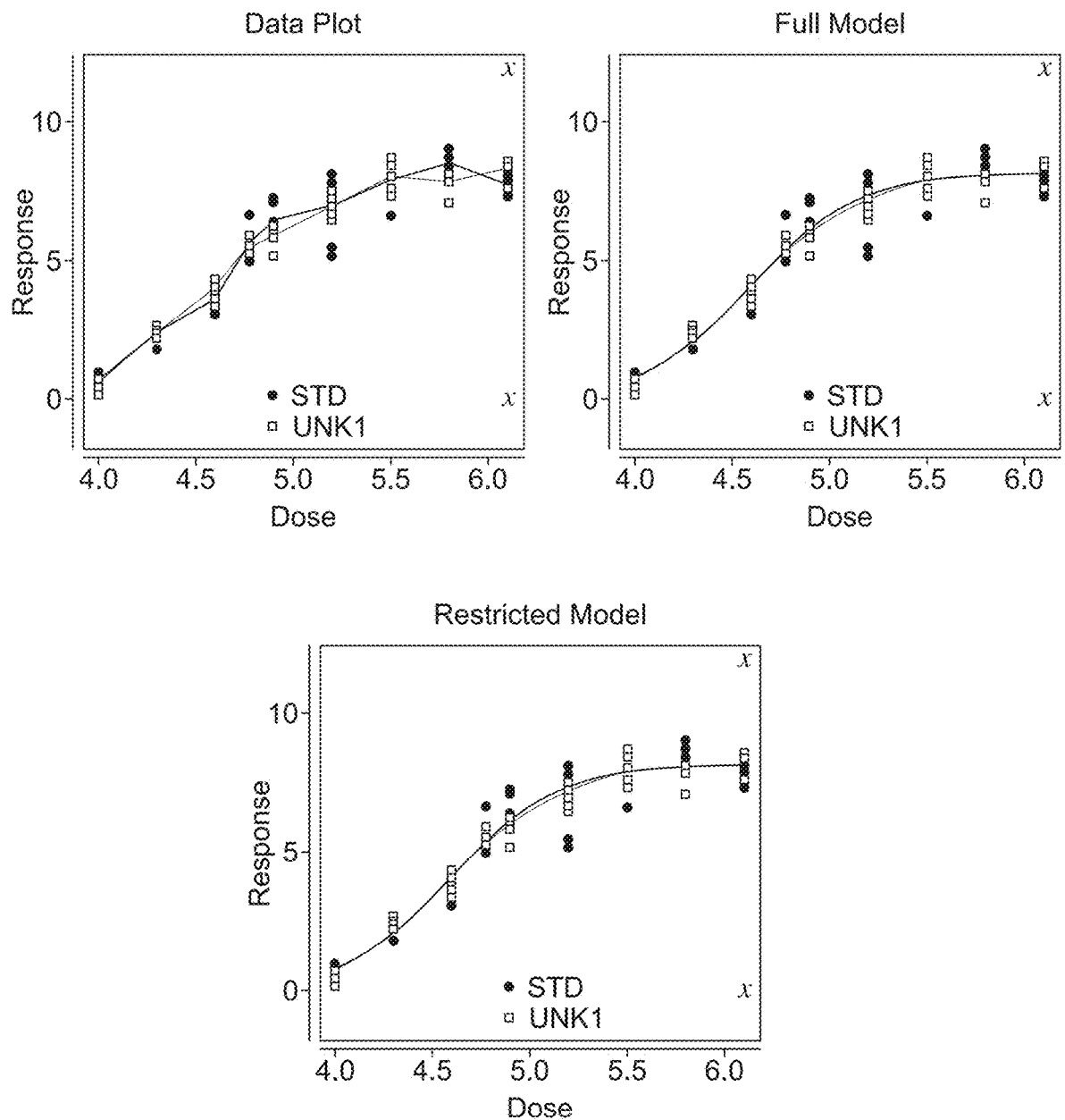
FIG. 16 shows PLA 3.0 Dose Response Curves for AAV2-hRPE65v2 Reference Standard (Dark) and Test Article Day 1, Analyst 1, 100% (Light) from Assay 5.
Figure 17:
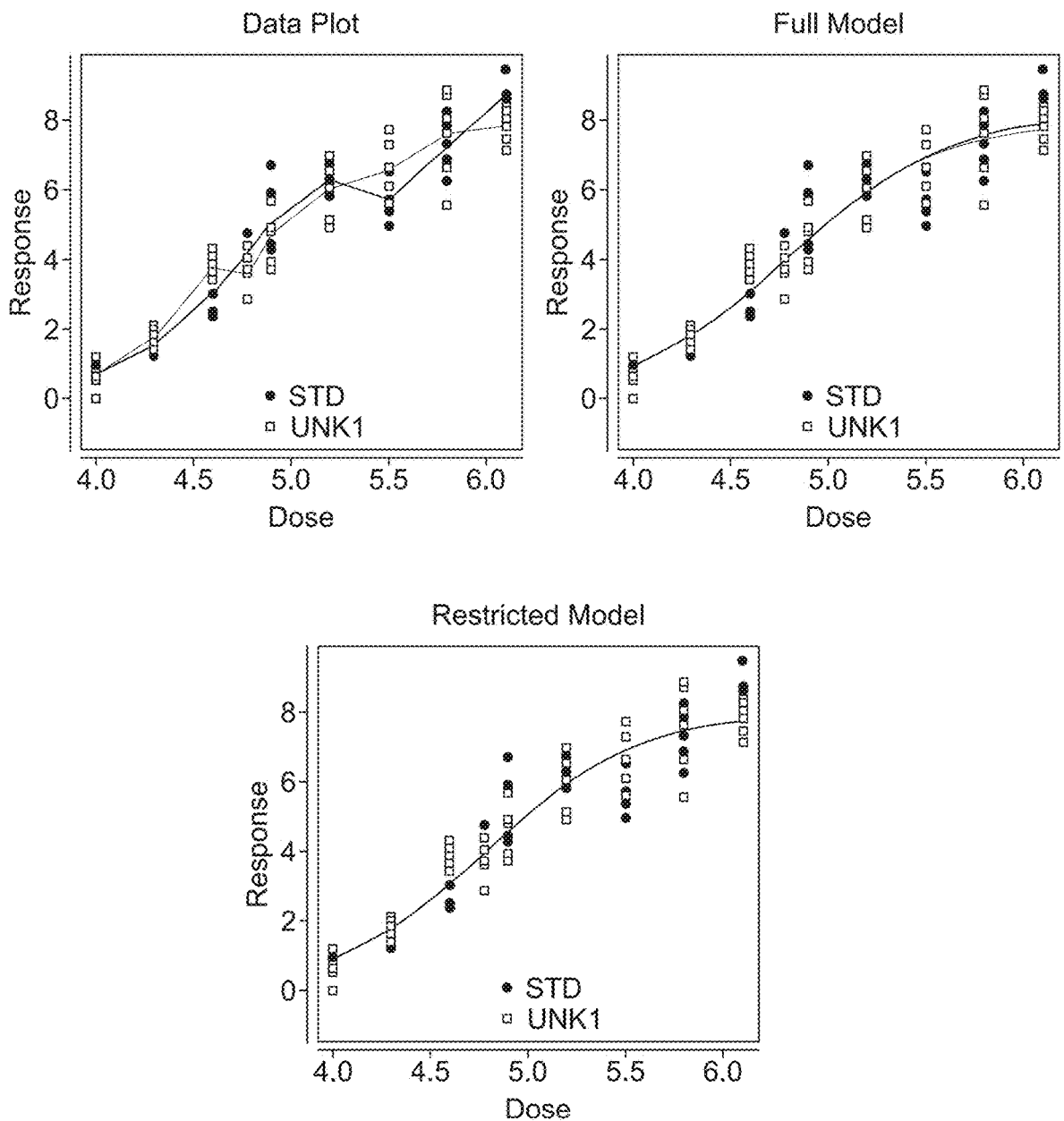
FIG. 17 shows PLA 3.0 Dose Response Curves for AAV2-hRPE65v2 Reference Standard (Dark) and Test Article Day 1, Analyst 2, 100% (Light) from Assay 6 Repeat.
Figure 18:
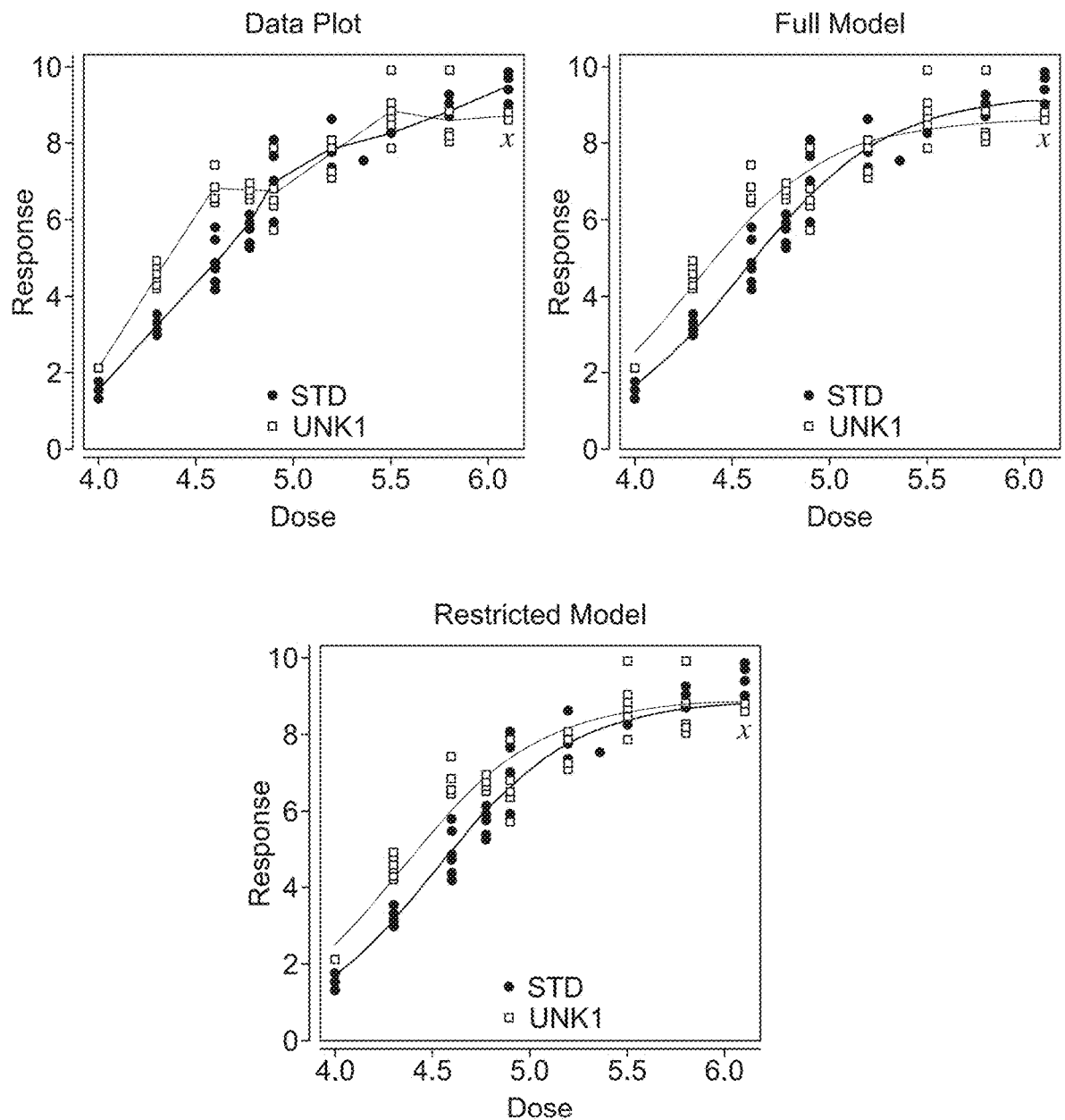
FIG. 18 shows PLA 3.0 Dose Response Curves for AAV2-hRPE65v2 Reference Standard (Dark) and Test Article Day 1, Analyst 1, 150% (Light) from Assay 9.
Figure 19:
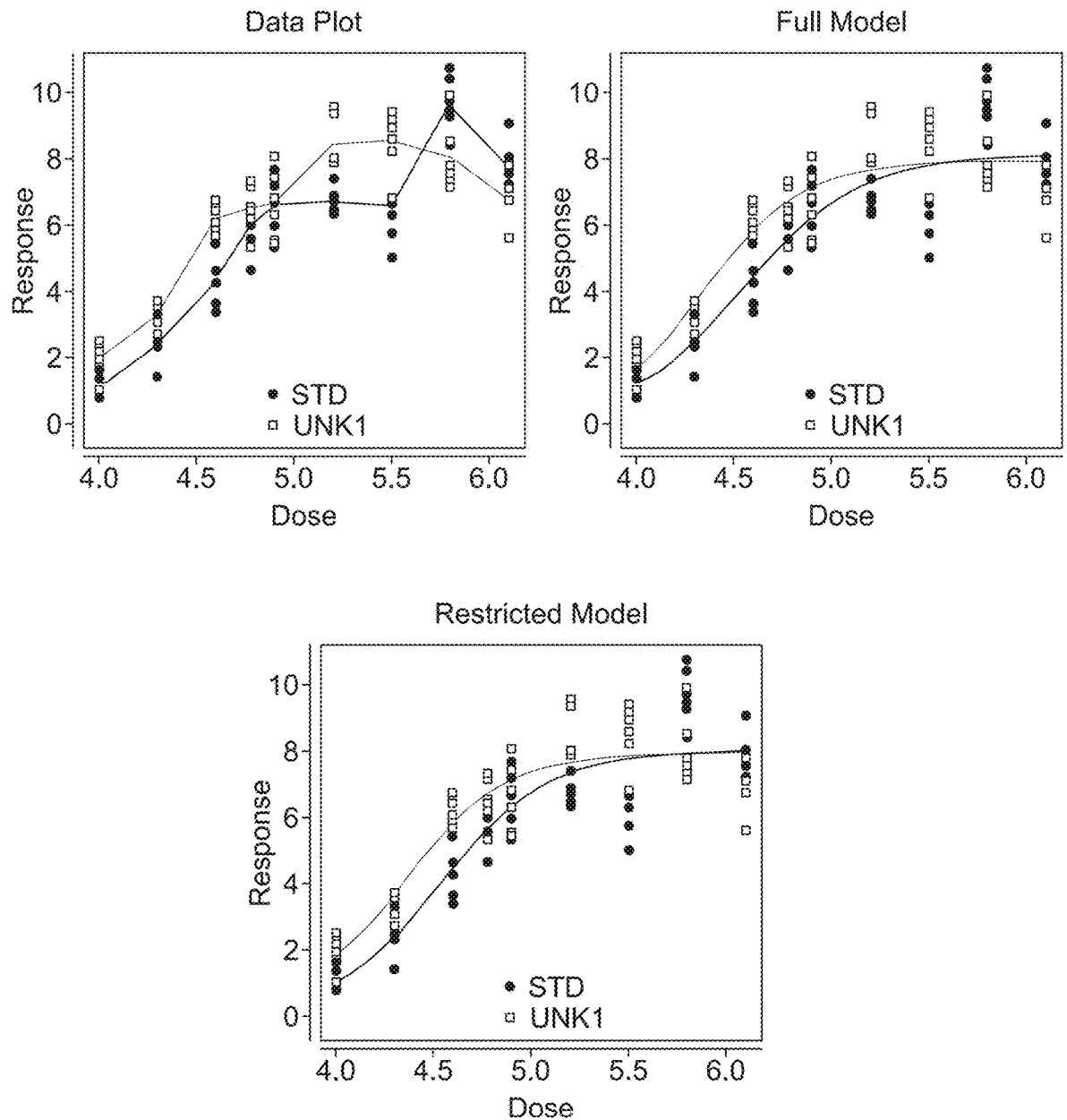
FIG. 19 shows PLA 3.0 Dose Response Curves for AAV2-hRPE65v2 Reference Standard (Dark) and Test Article Day 1, Analyst 2, 150% (Light) from Assay 10.

Point and 90% confidence interval estimates of relative bias are provided in the last 3 columns of Table 16. The point estimates for relative bias for three target levels are all within +/−25% which is the recommended validation acceptance criterion for relative accuracy given in Table 10. The 90% confidence intervals include zero at all three target level relative potencies. Thus from a statistical point of view, there is no evidence for bias at these three target levels. The relative bias estimates and their associated 90% confidence intervals are displayed in FIG. 13. All of the 90% intervals fall within the relative bias range of +/−30% which provides (for each target level separately) statistical tests at the 95% confidence level that the relative bias is within +/−30%.

PLA 3.0 Selected dose response curves for AAV2-hRPE65v2 Reference Standard and Test Article for three different levels (50%, 100% and 150%) for analyst 1 and analyst 2 are shown in FIG. 14 through FIG. 19.

between the value that is accepted either as a conventional true value or an accepted reference value and the value found.
Experimental Design The relative accuracy (calculated as the relative bias) was calculated at each concentration, using the relative potency values obtained from the intermediate precision testing.
Acceptance Criteria
Results, Discussion and Conclusions The acceptance criteria were met. Relative accuracy results are reported in Table 16. Point and 90% confidence interval estimates of relative bias are provided in the last 3 columns of Table 16.

The point estimates for relative bias at each target level relative potency of 0.5 (50%), 1.0 (100%), and 1.5 (150%) is −0.6%, +0.3%, and +10.0% respectively and are all within +/−25% or −25%≤x≤+25%, which is the recommended validation acceptance criterion for relative accuracy given in Table 10.

All three 90% confidence intervals include zero; thus from a statistical point of view, there is no evidence for any bias at these three target levels. The relative bias estimates and their associated 90% confidence intervals are displayed in FIG. 13. All of the 90% intervals fall within the relative bias range of +/−30% which provides evidence (for each target level separately) from two one-sided statistical tests at the 95% confidence level that the relative bias is within +/−30%.
Range

TABLE 16

Estimation of Relative Bias for each Target Level Using the ln(RP) Values from Table 11.

| Target Level | Ave. ln(RP) | Std. Dev. ln(RP) | 90% CI for mean ln(RP) | | Geom. Mean | 90% CI for Geom. Mean RP | | Geom. % CV (% GCV) | Relative Bias (%) (The Point Estimates) | 90% CI for Relative Bias (%) | |
|---|---|---|---|---|---|---|---|---|---|---|---|
| 0.5 | −0.699 | 0.091 | −0.81 | −0.59 | 0.50 | 0.45 | 0.55 | 9.5 | −0.6 | −10.7 | 10.6 |
| 1 | 0.003 | 0.094 | −0.09 | 0.08 | 1.00 | 0.92 | 1.08 | 9.9 | 0.3 | −8.4 | 8.3 |
| 1.5 | 0.501 | 0.144 | 0.33 | 0.64 | 1.65 | 1.39 | 1.89 | 15.5 | 10.0 | −7.1 | 26.2 |

TABLE 17

Estimation of Overall % GCV Across All Three Target Levels Based on the ln(RP) and Target Levels in Table 11

| Assay | ln(RP) − ln(Target) |
|---|---|
| 1 | −0.036 |
| 2-Repeat | −0.119 |
| 3 | 0.042 |
| 4 | 0.087 |
| 5 | −0.024 |
| 6-Repeat | 0.016 |
| 7 | 0.132 |
| 8 | 0.018 |
| 13 | −0.130 |
| 9 | 0.003 |
| 10 | 0.038 |
| 11 | 0.030 |
| 12 | 0.310 |
| Average on log scale | 0.028 |
| Standard Deviation on log scale | 0.107 |
| % GCV | 11.28 |

Relative Accuracy
Definition

The accuracy of an analytical method is the extent to which the test results generated by the method agree with the true value. Accuracy expresses the closeness of agreement Definition The range of the analytical method describes the interval between the upper and lower concentration, for which it has been demonstrated that the analytical method has a suitable level of precision, accuracy, and linearity.
Experimental Design The analysis and conclusions derived from the assessment of the intermediate precision, relative accuracy and dilutional linearity were used to establish the range over which results can be reliably reported.
Acceptance Criteria
Results, Discussion and Conclusions The range of 50% to 150% of the nominal method concentration, 9 MOI (1.00E+04, 2.00E+04, 4.00E+04, 6.00E+04, 8.00E+04, 1.60E+05, 3.20E+05, 6.40E+05, 1.28E+06) is supported by the linearity, accuracy, and precision data. Results supporting the range are reported in the Relative Accuracy, Intermediate Precision, and Dilutional Linearity Sections of this report.
Recommendations for Changes to the Data Analysis The PLA assay and sample suitability limits (margins) were re-examined after the isomerohydrolase activity assay qualification. Table 18 provides an evaluation of PLA suitability tests and limits based on both the 13 Qualification assays in Table 11 and on 4 additional pre-qualification assays (Assays 16, 19, 20, and 21) which were run with the same number and level of MOIs and analyzed using the same PLA template as used for qualification analyses.

TABLE 18

Re-examination of PLA Assay and Sample Suitability Limits (Margins)

| Test Type | PLA Suitability Test | Range of values observed from the 13 qualification and 4 pre-qualification Assay suitability tests | | Margins applied for qualification assays | | | Margins recommended based on 95% confidence one-sided tolerance bounds to contain 99.73% of future values | | |
|---|---|---|---|---|---|---|---|---|---|
| | | Min. | Max. | Severity | Lower | Upper | Severity | Lower | Upper |
| Sample Suitability Tests | Equivalence Test (Difference of Parameter Estimates): Upper asymptote UNK1, STD | −1.61 | 1.01 | Inf | −2.6 | 2.6 | Reject | −2.8 | 2.8 |
| | Equivalence Test (Difference of Parameter Estimates): Slope UNK1, STD | −1.96 | 2.48 | Warn | −7.1 | 7.1 | Reject | −3.6 | 3.6 |
| | Equivalence Test (Ratio of Parameter Estimates): Slopes UNK1, STD | 0.59 | 3.69 | Inf | 0.23 | 4.20 | Not used | | |
| | Equivalence Test (Ratio of Parameter Estimates): Upper asymptote UNK1, STD | 0.79 | 1.14 | Inf | 0.71 | 1.40 | Not used | | |
| | Additional Test: Sum of Squares of Non-Parallelism UNK1, STD | | 15.44 | Inf | | 22.3 | Not used | | |
| Assay Suitability Tests | Equivalence Test (Single Parameter): Slope STD | 0.78 | 5.42 | Inf | 0.23 | 9.00 | Reject | 0.23 | 9.00 |
| | Equivalence Test (Single Parameter): C-Parameter of the nonlinear model STD | 4.31 | 5.00 | Warn | 3.9 | 5.5 | Reject | 3.4 | 5.9 |
| | Equivalence Test (Single Parameter): Upper asymptote STD | 6.34 | 11.16 | Inf | 2.8 | 13.6 | Reject | 3.4 | 13.6 |
| | Additional Test: Maximal Number of Outliers STD | | 2 | Warn | | 5 | Reject | | 5 |
| | Additional Test: Minimal $R^2$ (Assay Element) STD | 0.84 | | Inf | 0.74 | | Inf | 0.74 | |
| | Equivalence Test (Single Parameter): Slope UNK1 | 0.83 | 5.92 | Inf | 0.23 | 9.00 | Reject | 0.23 | 9.00 |
| | Equivalence Test (Single Parameter): Upper asymptote UNK1 | 5.59 | 10.64 | Inf | 2.8 | 13.6 | Reject | 3.4 | 13.6 |
| | Equivalence Test (Single Parameter): C-Parameter of the nonlinear model UNK1 | 4.00 | 5.27 | Inf | 3.9 | 5.5 | Not used | | |
| | Additional Test: Maximal Number of Outliers UNK1 | | 2 | Warn | | 5 | Reject | | 5 |
| | Additional Test: Minimal $R^2$ (Assay Element) UNK1 | 0.79 | | Inf | 0.74 | | Inf | 0.74 | |
| | Additional Test: Sum of Squares of Non-Linearity UNK1, STD | | 61.73 | Inf | | 135 | Reject | | 90 |
| | Additional Test: elative Potency Range (%) UNK1 width of 90% CI relative to point estimate) | | 37.81% | Inf | | 40% | Inf | | 60% |
| Potency Estimation | Relative Potency UNK1 STD (90% CI relative to point estimate) | 82.9% | 120.7% | Inf | | | Inf | 76% | 130% |

Table 18 lists the 18 PLA test names analyzed in each of the 17 assays and the following analysis:
1. Observed statistic minimum and maximum values of each test statistic
2. The "severity level" and margins for each test applied during the qualification study.
3. The "severity level" and margins for each test recommended based on one-sided lower and upper 95% confidence tolerance limits to contain 99.73% of future test statistic values.

The severity codes in Table 18 give the action to be taken based in the event of a test failure:
Inf=Information only and no action taken,
Warn=Warning issued,
Rej=Sample/Assay rejected no report issued.

Because of analytical errors, Assays 2 and 6 needed to be re-run. These are indicated "2-Repeat" and "6-Repeat" in Table 11. The original assays 2 and 6 are not included in the present suitability test margin re-examination.

The suitability test margins (limits) used during the qualification study were established based on a limited number of pre-qualification assays. The qualification data, plus data from representative pre-qualification assays provide a much richer and more reliable base from which to estimate proper suitability test margins going forward.

With pre-qualification assay 16, the highest MOI (256K) was removed for the present PLA analysis to reflect the qualification protocol. An examination of the observed suitability tests for these 4 pre-qualification assays shows that they exhibited essentially the same distribution of observed test statistics as did the qualification assays. Including these 4 additional assays should lead to a more informed and reliable decision about any adjustments to the PLA suitability tests.

All 13 qualification assays and 4 additional representative pre-qualification assays passed the qualification assay and sample suitability criteria in the PLA template used for relative potency estimation (i.e., the qualification margins in Table 18).

Future valid assays should pass the recommended suitability tests because the test limits were based on 17 assays that: a) experienced no known analytical exceptions, b) had relative potency target levels within 0.5 to 1.5, and c) had standard and test samples derived from the same material and therefore the test sample is by definition, suitable. The margins based on tolerance bounds in the last 2 columns are conservative estimates of PLA limits that should provide a reasonable low probability of accidently failing an assay or sample merely because of random fluctuation in data.

All Equivalence tests in Table 18 are conducted at the 95% confidence level employing 90% confidence intervals. The recommended margins in the last 2 columns of Table 18 are based on tolerance bounds on key test statistics from the 17 assays. Tolerance intervals are based on either the observed lower, or observed upper 90% confidence interval. For additional tests, tolerance intervals are based on the point estimates of the respective test parameter.

In setting the recommended margins in Table 18, some tests were considered redundant and not recommended. Tests based on parameter ratios were redundant to those based on differences and serve no purpose. Similarly, the test for SSQ of non-parallelism is considered redundant since equivalence tests for Hill coefficients and upper asymptotes are already present. A test based on the C-parameter of the UNK was considered unnecessary because it is directly related to the relative potency of the UNK, the assay reportable result, which is controlled by product acceptance limits.

For the most part, the recommended margins in Table 18 do not differ greatly from those used in the qualification study. Some specific comments follow:

The final 2 tests in Table 18 supplement the Relative Potency estimate and are not really suitability tests. They are therefore included for information only.

No change in the maximum number of outliers permitted (5) is recommended.

No change in the equivalence assay suitability test for "slope". (Note here that PLA uses the word "slope" to indicate the Hill coefficient which is related to, but not equal to the slope of the profile at EC50).

When the one sided lower tolerance bound for a statistic that should be strictly positive (e.g., slope) is negative, a reasonable positive lower margin was chosen. As an example, the recommended lower margin for slope used for qualification (0.23) was retained.

Because the reference and test sample are expected to have the same upper asymptotes, slopes, and regression R-squares, the margins for these were obtained by combining the statistics for both sample types over all 17 assays.

Qualification Summary

All described experiments met the system suitability and sample acceptance criteria that were described in all the SOPs. The method was shown to be suitable for its intended purpose.

What is claimed is:

1. A method for measuring isomerohydrolase activity, wherein the method is linear from about $1\times10^4$ to about $2\times10^6$ AAV vector genomes per cell, comprising:
   (a) contacting cells expressing Lecithin Retinol Acyltransferase (LRAT) with an adeno-associated viral (AAV) vector genomes comprising a transgene encoding an isomerohydrolase protein under conditions allowing cell transduction;
   (b) incubating transduced cells under conditions allowing expression of the encoded isomerohydrolase protein;
   (c) collecting and lysing the transduced cells to produce an extract comprising the encoded isomerohydrolase protein;
   (d) incubating said extract with a substrate for a period of time and under conditions allowing conversion of the substrate by the isomerohydrolase protein to a 11-cis-retinol reaction product;
   (e) subjecting said 11-cis-retinol reaction product to column chromatography thereby producing a column chromatography purified 11-cis-retinol reaction product; and
   (f) subjecting said column chromatography purified 11-cis-retinol reaction product to mass spectrometry thereby quantifying the 11-cis-retinol reaction product, wherein the amount of the reaction product reflects isomerohydrolase activity thereby measuring isomerohydrolase activity, wherein the method is linear from about $1\times10^4$ to about $2\times10^6$ AAV vector genomes per cell.

2. The method of claim 1, wherein the isomerohydrolase protein comprises retinal pigment epithelium-specific protein, 65-KD (RPE6S).

3. The method of claim 1, wherein the isomerohydrolase protein comprises wild type retinal pigment epithelium-specific protein, 65-KD (RPE6S).

4. The method of claim 1, wherein the isomerohydrolase protein comprises a variant or mutant retinal pigment epithelium-specific protein, 65-KD (RPE65).

5. The method of claim 1, wherein the isomerohydrolase protein comprises a mammalian retinal pigment epithelium-specific protein, 65-KD (RPE6S).

6. The method of claim 1, wherein the isomerohydrolase protein comprises a human retinal pigment epithelium-specific protein, 65-KD (RPE6S).

7. The method of claim 1, wherein the cells comprise mammalian cells.

8. The method of claim 1, wherein the cells comprise human cells.

9. The method of claim 1, wherein the cells comprise Human Embryonic Kidney (HEK) 293 cells.

10. The method of claim 1, wherein the cells express LRAT stably or transiently.

11. The method of claim 1, wherein the substrate comprises all-trans-retinyl ester.

12. The method of claim 1, wherein step (d) comprises adding a precursor of the substrate to the extract, wherein the precursor is converted to said substrate by the expressed LRAT.

13. The method of claim 1, wherein step (d) comprises adding cellular retinaldehyde binding protein (CRALBP) and a precursor of the substrate to the extract, wherein the precursor is converted to said substrate by the expressed LRAT.

14. The method of claim 13, wherein the amount of CRALBP added is between about 50 and about 500 mg.

15. The method of claim 1, wherein the cells also stably or transiently express a cellular retinaldehyde binding protein (CRALBP).

16. The method of claim 12, wherein the precursor comprises or consists of all-trans retinol.

17. The method of claim 16, wherein the all-trans retinol is added such that the final concentration is about 1 to about 20 mM.

18. The method of claim 1, wherein step (d), (e) and/or (f) is performed in the dark, under dim light or under dim yellow light.

19. The method of claim 1, wherein the period of time of step (d) is from about 30 minutes to about 240 minutes.

20. The method of claim 1, wherein after step (d) but before step (e) the reaction is stopped or quenched.

21. The method of claim 1, wherein after step (d) but before step (e) an alcohol is added.

22. The method of claim 1, wherein step (d) further comprises extracting said 11-cis-retinol reaction product.

23. The method of claim 22, wherein said 11-cis-retinol reaction product is extracted with an organic solvent.

24. The method of claim 22, wherein said 11-cis-retinol reaction product is extracted with hexane.

25. The method of claim 1, wherein the adeno-associated viral (AAV) vector comprises a capsid protein sequence or inverted terminal repeat sequence having 70% or more sequence identity to a capsid protein sequence or to an inverted terminal repeat sequence of any serotype selected from AAV1, AAV2, AAV3, AAV4, AAVS5, AAV6, AAV7, AAV8, AAV9, and AAV10.

26. The method of claim 1, wherein the adeno-associated viral (AAV) vector comprises a capsid protein or inverted terminal repeat of any serotype selected from AAV1, AAV2, AAV3, AAV4, AAV5, AAV6, AAV7, AAV8, AAV9, AAV10.

27. The method of claim 1, wherein the (a) contacting cells is with an amount of about 500 to about 5 million AAV vector genomes/cell.

28. The method of claim 1, wherein the (a) contacting cells is with an amount of about 1,000 to about 1,000,000 AAV vector genomes/cell.

29. The method of claim 1, wherein the (a) contacting cells is with an amount of about 2,000 to about 500,000 AAV vector particles/cell.

30. The method of claim 1, wherein the (b) incubating the transduced cells is for a time period from about 6 hours to about 96 hours.

31. The method of claim 1, wherein the lysing the transduced cells of (c) is by freeze-thawing, sonication or a combination thereof.

32. The method of claim 1, wherein the amount of total cellular protein produced after step (c) is determined.

33. The method of claim 1, wherein the amount of total cellular protein produced after step (c) is determined by a Bradford assay.

34. The method of claim 12, wherein the precursor is mixed with a 10-100% solution of DMF.

35. The method of claim 1, wherein after collecting cells but prior to (c) lysing, the collected cells are resuspended in buffer.

36. The method of claim 1, wherein after (c) lysing the transduced cells to produce an extract the extract is diluted in buffer.

37. The method of claim 35, wherein the buffer is a salt buffer.

38. The method of claim 35, wherein the buffer is a NaCl buffer.

39. The method of claim 1, wherein said extract produced by step (c) comprises from about 10 mg to about 2,000 mg total cellular protein or is adjusted to be from about 10 mg to about 2,000 mg total protein.

40. The method of claim 1, wherein said extract produced by step (c) comprises from about 50 mg to about 750 mg total cellular protein or is adjusted to be from about 50 mg to about 750 mg total protein.

41. The method of claim 1, wherein said (d) incubating is at a temperature from about 30° C. to about 40° C.

42. The method of claim 1, wherein the column chromatography separates 11-cis-retinol from 9-cis-retinol and/or separates 11-cis-retinol from 13-cis-retinol.

43. The method of claim 1, wherein the column chromatography comprises reverse-phase chromatography.

44. The method of claim 1, wherein the column chromatography comprises a reverse-phase stationary phase.

45. The method of claim 44, wherein the stationary phase comprises a C18 chain.

46. The method of claim 44, wherein the stationary phase comprises a hydrophilic group.

47. The method of claim 44, wherein the hydrophilic group comprises a carbamate group.

48. The method of claim 44, wherein the stationary phase comprises a hydrophilic carbamate group within a C18 chain.

49. The method of claim 44, wherein the stationary phase comprises a silylcarbamate group.

50. The method of claim 1, wherein the method comprises determining a coefficient of determination ($R^2$), wherein said coefficient of determination ($R^2$) is greater than about 0.85.

* * * * *

UNITED STATES PATENT AND TRADEMARK OFFICE
CERTIFICATE OF CORRECTION

PATENT NO. : 12,359,239 B2
APPLICATION NO. : 16/096673
DATED : July 15, 2025
INVENTOR(S) : Linda Couto Page 1 of 1

It is certified that error appears in the above-identified patent and that said Letters Patent is hereby corrected as shown below:

In the Claims

In Claim 2, at Column 45, Line 51: "RPE6S" should be corrected to --RPE65--
In Claim 3, at Column 45, Line 54: "RPE6S" should be corrected to --RPE65--
In Claim 5, at Column 45, Line 60: "RPE6S" should be corrected to --RPE65--
In Claim 6, at Column 45, Line 63: "RPE6S" should be corrected to --RPE65--

In Claim 14, at Column 46, Line 34: "mg" should be corrected to --µg--
In Claim 25, at Column 46, Line 64: "AAVS5" should be corrected to --AAV5--

In Claim 26, at Column 47, Line 2: "AAVS" should be corrected to --AAV5--

In Claim 39, at Column 48, Lines 2-4: each instance of "mg" should be corrected to --µg--
In Claim 40, at Column 48, Lines 6-8: each instance of "mg" should be corrected to --µg--

Signed and Sealed this
Twenty-third Day of September, 2025

John A. Squires
*Director of the United States Patent and Trademark Office*

SEQUENCE LISTING

<160> NUMBER OF SEQ ID NOS: 1

<210> SEQ ID NO 1
<211> LENGTH: 533
<212> TYPE: PRT
<213> ORGANISM: Homo sapiens

<400> SEQUENCE: 1

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

-continued

```
Leu Phe Glu Val Gly Ser Glu Pro Phe Tyr His Leu Phe Asp Gly Gln
 50                  55                  60

Ala Leu Leu His Lys Phe Asp Phe Lys Glu Gly His Val Thr Tyr His
 65                  70                  75                  80

Arg Arg Phe Ile Arg Thr Asp Ala Tyr Val Arg Ala Met Thr Glu Lys
                 85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
            115                 120                 125

Thr Asp Asn Ala Leu Val Asn Val Tyr Pro Val Gly Glu Asp Tyr Tyr
130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
            195                 200                 205

Ile Pro Pro Leu Gln Ala Asp Lys Glu Asp Pro Ile Ser Lys Ser Glu
210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
            275                 280                 285

Leu His Ile Ala Asp Lys Lys Arg Lys Lys Tyr Leu Asn Asn Lys Tyr
290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
            355                 360                 365

Val Leu Pro Leu Asn Ile Asp Lys Ala Asp Thr Gly Lys Asn Leu Val
370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
            435                 440                 445

Lys Leu Asn Val Lys Thr Lys Glu Thr Trp Val Trp Gln Glu Pro Asp
450                 455                 460
```

```
Ser Tyr Pro Ser Glu Pro Ile Phe Val Ser His Pro Asp Ala Leu Glu
465                 470                 475                 480

Glu Asp Asp Gly Val Val Leu Ser Val Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530
```